United States Patent
Björk et al.

(10) Patent No.: US 8,193,363 B2
(45) Date of Patent: Jun. 5, 2012

(54) COMPOUNDS SUITABLE AS PRECURSORS TO COMPOUNDS THAT ARE USEFUL FOR IMAGING AMYLOID DEPOSITS

(75) Inventors: Seth Björk, Södertälje (SE); Peter Johnström, Södertälje (SE); Nils Anders Nilsson, Södertälje (SE); Katinka Ruda, Södertälje (SE); Per Magnus Schou, Södertälje (SE); Britt-Marie Swahn, Södertälje (SE); Vern Delisser, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 379 days.

(21) Appl. No.: 12/544,556

(22) Filed: Aug. 20, 2009

(65) Prior Publication Data

US 2010/0056796 A1     Mar. 4, 2010

Related U.S. Application Data

(60) Provisional application No. 61/092,851, filed on Aug. 29, 2008.

(51) Int. Cl.
*C07D 405/04* (2006.01)
(52) U.S. Cl. .................................................. 546/284.1
(58) Field of Classification Search ................ 546/284.1
See application file for complete search history.

(56) References Cited

U.S. PATENT DOCUMENTS 7,772,256 B2 *    8/2010    Arzel et al. ................... 514/337

* cited by examiner

*Primary Examiner* — Patricia Morris
(74) *Attorney, Agent, or Firm* — David Gryte

(57) ABSTRACT

The present invention relates to novel derivatives that are suitable as precursors to compounds that are useful for imaging amyloid deposits in living patients, their compositions, methods of use and processes to make such compounds. The compounds deriving from these precursors are useful in methods of imaging amyloid deposits in brain in vivo to allow antemortem diagnosis of Alzheimer's disease by positron emission tomography (PET) as well as measuring clinical efficacy of Alzheimer's disease therapeutic agents. Furthermore, the present invention also discloses the precursor compounds in crystalline form.

5 Claims, 3 Drawing Sheets

Figure 1. X-ray powder diffraction pattern of compound I.
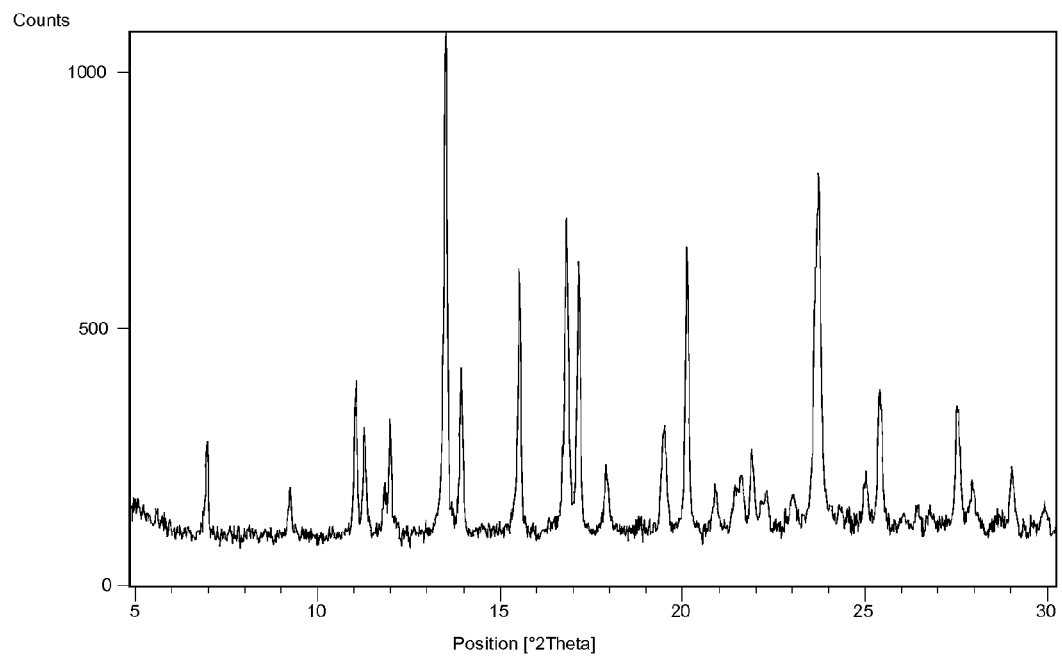
Figure 2. X-ray powder diffraction pattern of compound I.
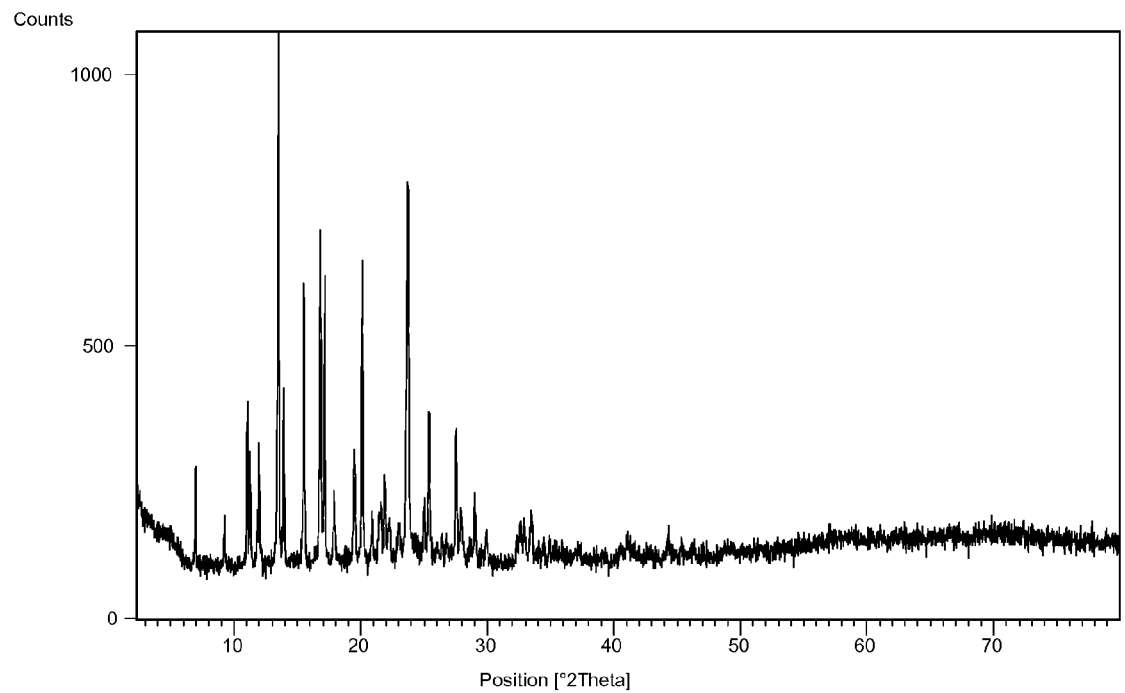

Figure 3. X-ray powder diffraction pattern of compound II.
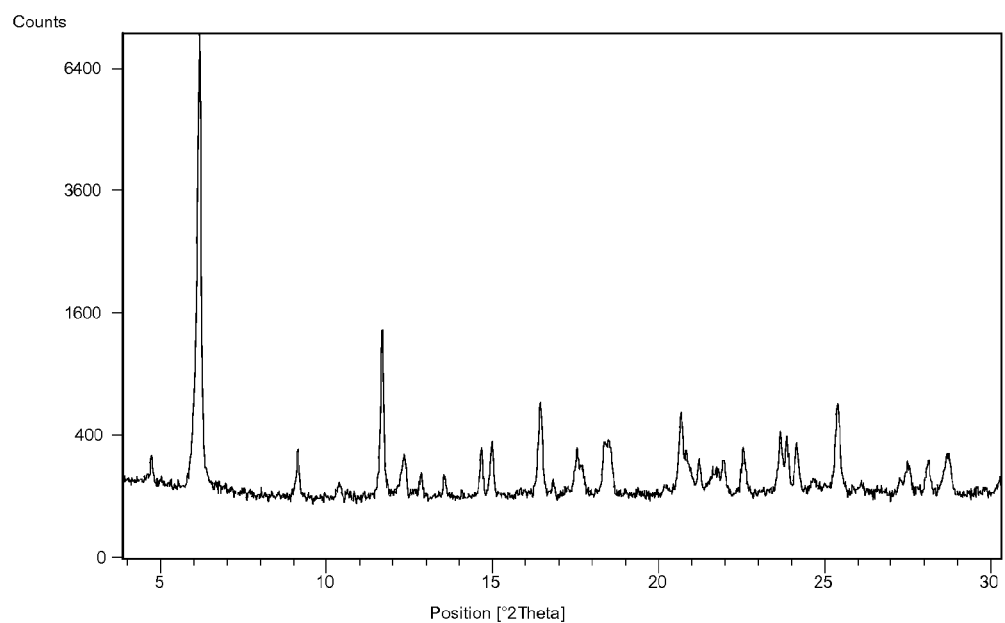
Figure 4. X-ray powder diffraction pattern of compound II.
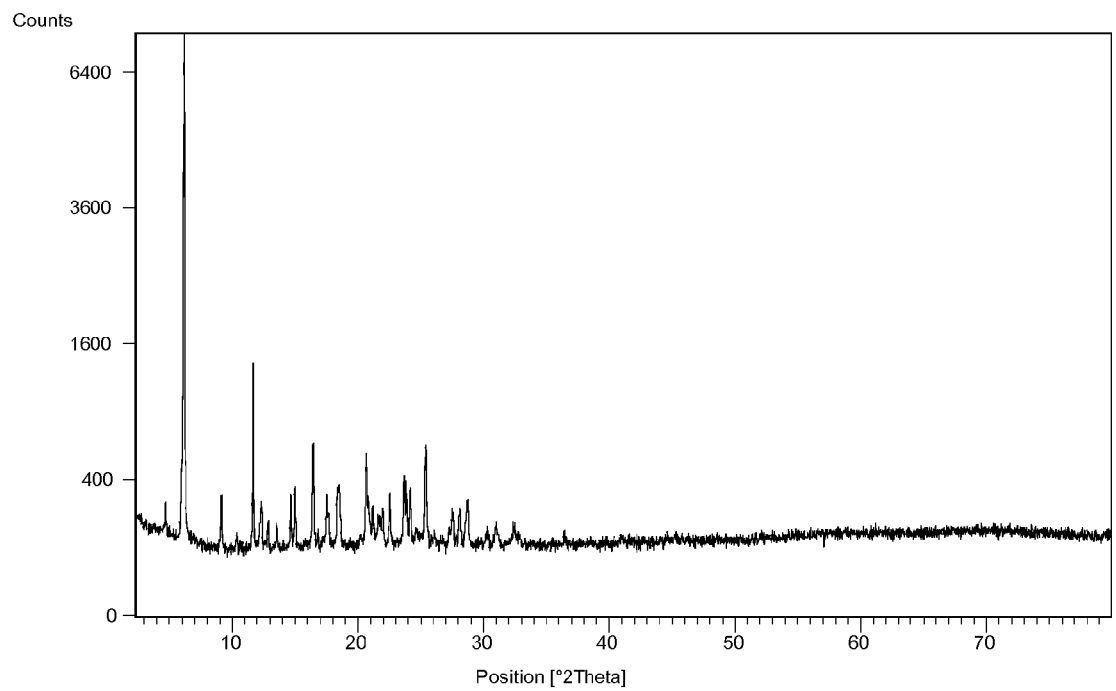

Figure 5. X-ray powder diffraction patterns of compound I (A); compound II (B); Sodium sulphate (C); and Sodium chloride (D)
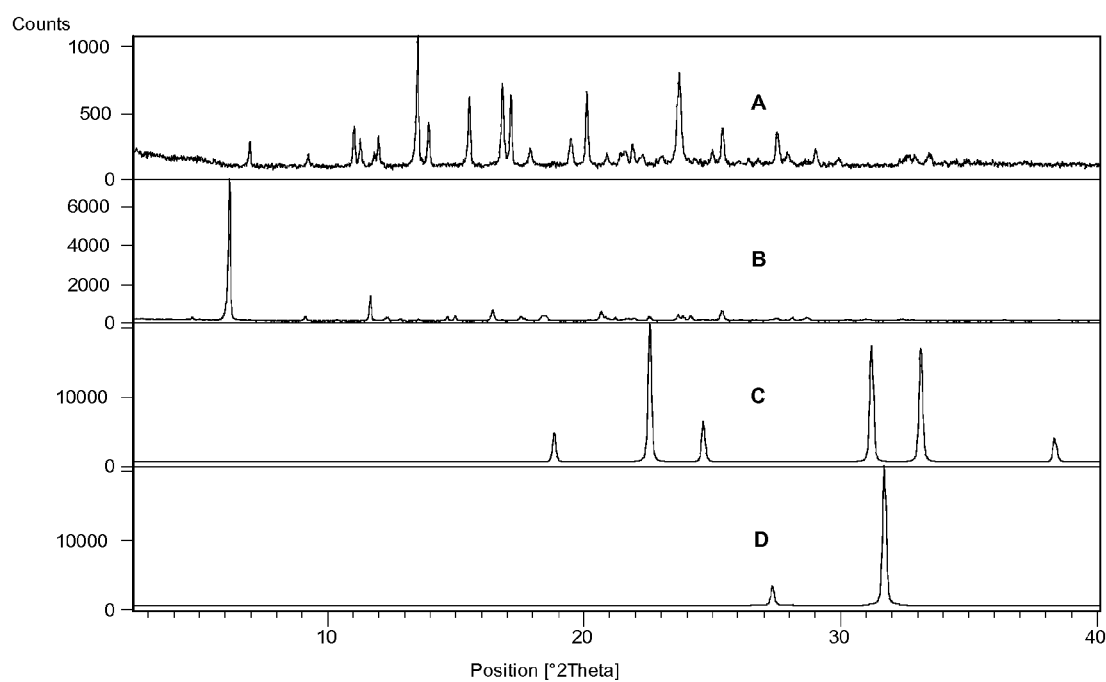

COMPOUNDS SUITABLE AS PRECURSORS TO COMPOUNDS THAT ARE USEFUL FOR IMAGING AMYLOID DEPOSITS

This patent claims the benefit of to U.S. Provisional Application No. 61/092,851 (filed 29 Aug. 2008). The entire text of the above-referenced patent application is incorporated by reference into this patent.

The present invention relates to novel derivatives that are suitable as precursors to compounds useful for imaging amyloid deposits in mammals such as living patients, their compositions, methods of use and processes to make such compounds. The compounds deriving from these precursors are useful in methods of imaging amyloid deposits in the brain in vivo to allow antemortem diagnosis of Alzheimer's disease with imaging techniques such as positron emission tomography (PET). The compounds can also be used for measuring clinical efficacy of Alzheimer's disease therapeutic agents. Furthermore, the present invention also discloses the precursor compounds in crystalline form.

Amyloidosis is a progressive, incurable metabolic disease of unknown cause characterized by abnormal deposits of protein in one or more organs or body systems. Amyloid proteins are manufactured, for example, by malfunctioning bone marrow. Amyloidosis, which occurs when accumulated amyloid deposits impair normal body function, can cause organ failure or death. It is a rare disease, occurring in about eight of every 1,000,000 people. It affects males and females equally and usually develops after the age of 40. At least 15 types of amyloidosis have been identified. Each one is associated with deposits of a different kind of protein.

The major forms of amyloidosis are primary systemic, secondary, and familial or hereditary amyloidosis.

There is also another form of amyloidosis, which is associated with Alzheimer's disease. Primary systemic amyloidosis usually develops between the ages of 50 and 60. With about 2,000 new cases diagnosed annually, primary systemic amyloidosis is the most common form of this disease in the United States. Also known as light-chain-related amyloidosis, it may also occur in association with multiple myeloma (bone marrow cancer). Secondary amyloidosis is a result of chronic infection or inflammatory disease. It is often associated with Familial Mediterranean fever (a bacterial infection characterized by chills, weakness, headache, and recurring fever), Granulomatous ileitis (inflammation of the small intestine), Hodgkin's disease, Leprosy, Osteomyelitis and Rheumatoid arthritis.

Familial or hereditary amyloidosis is the only inherited form of the disease. It occurs in members of most ethnic groups, and each family has a distinctive pattern of symptoms and organ involvement. Hereditary amyloidosis is though to be autosomal dominant, which means that only one copy of the defective gene is necessary to cause the disease. A child of a parent with familial amyloidosis has a 50-50 risk of developing the disease.

Amyloidosis can involve any organ or system in the body. The heart, kidneys, gastrointestinal system, and nervous system are affected most often. Other common sites of amyloid accumulation include the brain, joints, liver, spleen, pancreas, respiratory system, and skin.

Alzheimer's disease (AD) is the most common form of dementia, a neurologic disease characterized by loss of mental ability severe enough to interfere with normal activities of daily living, lasting at least six months, and not present from birth. AD usually occurs in old age, and is marked by a decline in cognitive functions such as remembering, reasoning, and planning.

Between two and four million Americans have AD; that number is expected to grow to as many as 14 million by the middle of the 21st century as the population as a whole ages. While a small number of people in their 40s and 50s develop the disease, AD predominantly affects the elderly. AD affects about 3% of all people between ages 65 and 74, about 20% of those between 75 and 84, and about 50% of those over 85.

The accumulation of amyloid Aβ-peptide in the brain is a pathological hallmark of all forms of AD. It is generally accepted that deposition of cerebral amyloid Aβ-peptide is the primary influence driving AD pathogenesis. (Hardy J and Selkoe D. J., Science. 297: 353-356, 2002).

Imaging techniques, such as positron emission tomography (PET) and single photon emission computed tomography (SPECT), are effective in monitoring the accumulation of amyloid deposits in the brain and useful techniques for measuring the correlation to the progression of AD (see e.g. Miller, Science, 2006, 313, 1376). The application of these techniques requires radioligands that readily enter the brain and selectively bind to amyloid deposits in vivo.

A need exists for amyloid binding compounds that can cross the blood-brain barrier, and consequently, can be used in diagnostics. Furthermore, it is important to monitor the efficacy of the treatment given to AD patients, by measuring the effect of said treatment by measuring changes of AD plaque levels.

Properties of particular interest of a detectable amyloid-binding compound, besides high affinity for amyloid deposits in vivo and high and rapid brain entrance, include low unspecific binding to normal tissue and rapid clearance from the same. These properties are commonly dependant on the lipophilicity of the compound (Coimbra et al. Curr. Top. Med. Chem. 2006, 6, 629). Among the proposed small molecules for imaging amyloid plaques, some uncharged analogs of thioflavin T have been synthesized (Mathis et al. J. Med. Chem. 2003, 46, 2740). Different isosteric heterocycles are reported as potential amyloid binding ligands (Cai et al. J. Med. Chem. 2004, 47, 2208; Kung et al. J. Med. Chem. 2003, 46, 237). Benzofuran derivatives have previously been described for use as amyloid imaging agents (Ono et al. J. Med. Chem. 2006, 49, 2725; Lockhart et al. J. Biol. Chem. 2005, 280(9), 7677; Kung et al. Nuclear Med. Biol. 2002, 29(6), 633; WO2003051859 and for use in preventing Abeta aggregation (Twyman et al. Tetrahedron Lett. 1999, 40(52), 9383; Howlett et al. Biochemical Journal 1999, 340(1), 283; Choi et al. Archives of Pharmacal Research 2004, 27(1), 19; Twyman et al. Bioorg. Med. Chem. Lett. 2001, 11(2), 255; WO9517095).

In one embodiment of the present invention, there is provided [6-(5-Ethoxymethoxy-benzofuran-2-yl)-2-nitro-pyridin-3-yl]-methyl-carbamic acid tert-butyl ester or salts thereof. In another embodiment the salt is a pharmaceutically acceptable salt. In a further embodiment of the present invention, there is provided the compound [5-(5-Ethoxymethoxy-benzofuran-2-yl)-6-nitro-pyridin-2-yl]-methyl-carbamic acid tert-butyl ester or salt thereof. In another embodiment the salt is a pharmaceutically acceptable salt.

The chemical structures of these compounds are:

I

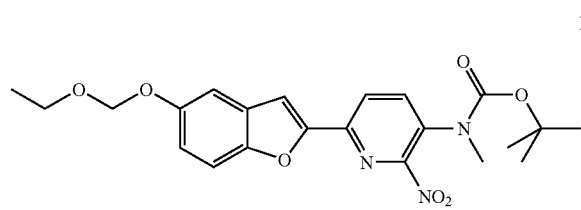

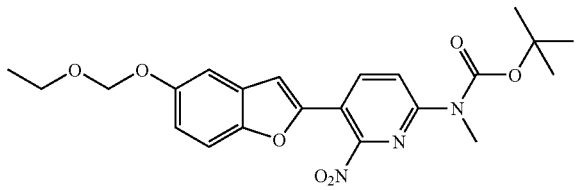

Compound I refers to [6-(5-Ethoxymethoxy-benzofuran-2-yl)-2-nitro-pyridin-3-yl]-methyl-carbamic acid tert-butyl ester and compound II refers to [5-(5-Ethoxymethoxy-benzofuran-2-yl)-6-nitro-pyridin-2-yl]-methyl-carbamic acid tert-butyl ester.

A compound can be expected to be more stable chemically in a crystalline state in comparison with the same compound in an amorphous state, as described in Haleblian and McCrone J. Pharm. Sci 1969, 58, p 911-929, especially p 913. This observation is common for small molecules (i.e. non-proteins) but not always true for macromolecules like proteins, as described in Pikal and Rigsbee, Pharm. Res. 1997, 14, p 1379-1387, especially p 1379. A crystalline state is thus beneficial for small molecules such as [6-(5-Ethoxymethoxy-benzofuran-2-yl)-2-nitro-pyridin-3-yl]-methyl-carbamic acid tert-butyl ester and (5-Bromo-6-nitro-pyridin-2-yl)-methyl-carbamic acid tert-butyl ester respectively.

X-rays will be scattered by electrons in atoms in a compound. Crystalline material will diffract X-rays giving peaks in directions of constructive interference. The directions are determined by the crystal structure, including the size and shape of the unit cell. All diffraction peak °2theta values disclosed and/or claimed herein refer to Cu Kα-radiation. An amorphous (non-crystalline) material will not give such diffraction peaks. See e.g. Klug, H. P. & Alexander, L. E., X-Ray Diffraction Procedures For Polycrystalline and Amorphous Materials, 1974, John Wiley & Sons.

The ability for a compound to lump together or cake without control will increase if the compound is heated to near its melting temperature. Lumps and cakes will have different flow and dissolution properties as compared with a powder. Mechanical treatment of a powder, such as during particle size reduction, will bring energy into the material and thus give a possibility to raise the temperature. Storage of a compound as well as transport of a compound can unintentionally also lead to an increased temperature.

Melting is an endothermic event. Endothermic events can be measured by, e.g. differential scanning calorimetry.

It is thus beneficial for [6-(5-Ethoxymethoxy-benzofuran-2-yl)-2-nitro-pyridin-3-yl]-methyl-carbamic acid tert-butyl ester or salt thereof; and [5-(5-Ethoxymethoxy-benzofuran-2-yl)-6-nitro-pyridin-2-yl]-methyl-carbamic acid tert-butyl ester or salt thereof respectively to have such endothermic events at a temperature higher than the highest temperature expected during normal use to prevent said compounds from forming an undesired lump or cake.

In another embodiment of the present invention, there is provided [6-(5-Ethoxymethoxy-benzofuran-2-yl)-2-nitro-pyridin-3-yl]-methyl-carbamic acid tert-butyl ester or salt thereof; and [5-(5-Ethoxymethoxy-benzofuran-2-yl)-6-nitro-pyridin-2-yl]-methyl-carbamic acid tert-butyl ester or salt thereof, in crystalline form.

In another embodiment of the present invention, there is provided [6-(5-Ethoxymethoxy-benzofuran-2-yl)-2-nitro-pyridin-3-yl]-methyl-carbamic acid tert-butyl ester or salt thereof; and [5-(5-Ethoxymethoxy-benzofuran-2-yl)-6-nitro-pyridin-2-yl]-methyl-carbamic acid tert-butyl ester or salt thereof, in crystalline form, comprising distinct X-Ray diffraction peaks and having at least one endothermic event with onset between 70° C. and 300° C.

In another embodiment of the present invention, there is provided the compound [6-(5-Ethoxymethoxy-benzofuran-2-yl)-2-nitro-pyridin-3-yl]-methyl-carbamic acid tert-butyl ester or salt thereof, in crystalline form, having an X-ray powder diffraction pattern with at least one specific diffraction peak at about 2-theta=13.51°.

In another embodiment of the present invention, there is provided the compound [6-(5-Ethoxymethoxy-benzofuran-2-yl)-2-nitro-pyridin-3-yl]-methyl-carbamic acid tert-butyl ester or salt thereof, in crystalline form, comprising the following diffraction peaks: 11.27, 12.00, 13.51, 15.53, 16.82, 17.91 and 23.72°2theta.

In a further embodiment said crystalline form comprises the following diffraction peaks: 6.97, 9.24, 11.27, 12.00, 13.51, 15.53, 16.82, 17.91 and 23.72°2theta.

In another embodiment of the present invention, there is provided the compound [5-(5-Ethoxymethoxy-benzofuran-2-yl)-6-nitro-pyridin-2-yl]-methyl-carbamic acid tert-butyl ester or salt thereof, in crystalline form, having an X-ray powder diffraction pattern with at least one specific diffraction peak at about 2-theta=6.18°.

In another embodiment of the present invention, there is provided the compound [5-(5-Ethoxymethoxy-benzofuran-2-yl)-6-nitro-pyridin-2-yl]-methyl-carbamic acid tert-butyl ester or salt thereof, in crystalline form, comprising the following diffraction peaks: 6.18, 9.14, 11.67, 14.98 and 16.44°2theta.

In a further embodiment said crystalline form comprises the following diffraction peaks: 6.18, 9.14, 11.67, 12.32, 14.65, 14.98, 16.44, 17.52 and 20.66°2theta.

In another embodiment of the present invention, there is provided the use of [6-(5-Ethoxymethoxy-benzofuran-2-yl)-2-nitro-pyridin-3-yl]-methyl-carbamic acid tert-butyl ester or salt thereof and [5-(5-Ethoxymethoxy-benzofuran-2-yl)-6-nitro-pyridin-2-yl]-methyl-carbamic acid tert-butyl ester or salt thereof, as a synthetic precursor, in making a final compound useful for imaging amyloid deposits in mammals such as living patients. In one embodiment, [6-(5-Ethoxymethoxy-benzofuran-2-yl)-2-nitro-pyridin-3-yl]-methyl-carbamic acid tert-butyl ester or salt thereof or [5-(5-Ethoxymethoxy-benzofuran-2-yl)-6-nitro-pyridin-2-yl]-methyl-carbamic acid tert-butyl ester or salt thereof is in crystalline form. In a further embodiment said compounds have a diffraction pattern described above.

In another embodiment of the present invention, there is provided the use of [6-(5-Ethoxymethoxy-benzofuran-2-yl)-2-nitro-pyridin-3-yl]-methyl-carbamic acid tert-butyl ester or salt thereof or [5-(5-Ethoxymethoxy-benzofuran-2-yl)-6-nitro-pyridin-2-yl]-methyl-carbamic acid tert-butyl ester or salt thereof, as a synthetic precursor, in a process for the preparation of a labelled compound. In a further embodiment the label is an $^{18}$F atom. In one embodiment, [6-(5-Ethoxymethoxy-benzofuran-2-yl)-2-nitro-pyridin-3-yl]-methyl-carbamic acid tert-butyl ester or salt thereof or [5-(5-Ethoxymethoxy-benzofuran-2-yl)-6-nitro-pyridin-2-yl]-methyl-carbamic acid tert-butyl ester or salt thereof is in crystalline form. In a further embodiment said compounds have a diffraction pattern described above.

The compounds [6-(5-Ethoxymethoxy-benzofuran-2-yl)-2-nitro-pyridin-3-yl]-methyl-carbamic acid tert-butyl ester or salt thereof and [5-(5-Ethoxymethoxy-benzofuran-2-yl)-6-nitro-pyridin-2-yl]-methyl-carbamic acid tert-butyl ester or salt thereof are useful in the preparation of (radio)labeled compounds of the following formulas:

2-(6-Fluoro-5-methylamino-pyridin-2-yl)-benzofuran-5-ol

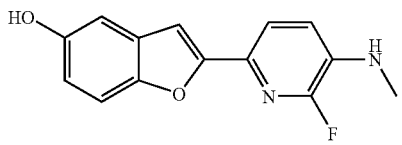

2-(2-Fluoro-6-methylamino-pyridin-3-yl)-benzofuran-5-ol

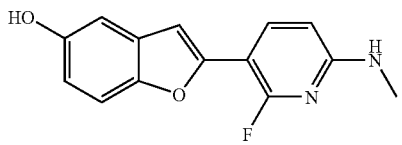

In one embodiment, [6-(5-Ethoxymethoxy-benzofuran-2-yl)-2-nitro-pyridin-3-yl]-methyl-carbamic acid tert-butyl ester or salt thereof or [5-(5-Ethoxymethoxy-benzofuran-2-yl)-6-nitro-pyridin-2-yl]-methyl-carbamic acid tert-butyl ester or salt thereof is in crystalline form. In a further embodiment said compounds have a diffraction pattern described above.

In another embodiment of the present invention, there is provided the use of [6-(5-Ethoxymethoxy-benzofuran-2-yl)-2-nitro-pyridin-3-yl]-methyl-carbamic acid tert-butyl ester or salt thereof or [5-(5-Ethoxymethoxy-benzofuran-2-yl)-6-nitro-pyridin-2-yl]-methyl-carbamic acid tert-butyl ester or salt thereof, in the preparation of compounds 2-(6-[$^{18}$F]-fluoro-5-methylamino-pyridin-2-yl)-benzofuran-5-ol and 2-(2-[$^{18}$F]-fluoro-6-methylamino-pyridin-3-yl)-benzofuran-5-ol.

In one embodiment, [6-(5-Ethoxymethoxy-benzofuran-2-yl)-2-nitro-pyridin-3-yl]-methyl-carbamic acid tert-butyl ester or salt thereof or [5-(5-Ethoxymethoxy-benzofuran-2-yl)-6-nitro-pyridin-2-yl]-methyl-carbamic acid tert-butyl ester or salt thereof is in crystalline form. In a further embodiment said compounds have a diffraction pattern described above.

In another embodiment the salt of [6-(5-Ethoxymethoxy-benzofuran-2-yl)-2-nitro-pyridin-3-yl]-methyl-carbamic acid tert-butyl ester and [5-(5-Ethoxymethoxy-benzofuran-2-yl)-6-nitro-pyridin-2-yl]-methyl-carbamic acid tert-butyl ester are pharmaceutically acceptable salts.

In one embodiment, said detection is carried out by a technique selected from gamma imaging, positron emission tomography (PET), magnetic resonance imaging and magnetic resonance spectroscopy.

BRIEF DESCRIPTION OF THE DRAWINGS

FIG. 1 depicts the X-ray powder diffraction pattern of [6-(5-Ethoxymethoxy-benzofuran-2-yl)-2-nitro-pyridin-3-yl]-methyl-carbamic acid tert-butyl ester. Vertical axis represents intensity (counts) and horizontal axis represents position (°2theta for Cu Kα-radiation).

FIG. 2 depicts the X-ray powder diffraction pattern of [6-(5-Ethoxymethoxy-benzofuran-2-yl)-2-nitro-pyridin-3-yl]-methyl-carbamic acid tert-butyl ester in a different scale at horizontal axis compared to FIG. 1. Vertical axis represents intensity (counts) and horizontal axis represents position (°2theta for Cu Kα-radiation).

FIG. 3 depicts the X-ray powder diffraction pattern of [5-(5-Ethoxymethoxy-benzofuran-2-yl)-6-nitro-pyridin-2-yl]-methyl-carbamic acid tert-butyl ester. Vertical axis represents intensity (counts) and horizontal axis represents position (°2theta for Cu Kα-radiation).

FIG. 4 depicts the X-ray powder diffraction pattern of [5-(5-Ethoxymethoxy-benzofuran-2-yl)-6-nitro-pyridin-2-yl]-methyl-carbamic acid tert-butyl ester in a different scale at horizontal axis compared to FIG. 1. Vertical axis represents intensity (counts) and horizontal axis represents position (°2theta for Cu Kα-radiation).

FIG. 5 depicts the X-ray powder diffraction patterns of [6-(5-Ethoxymethoxy-benzofuran-2-yl)-2-nitro-pyridin-3-yl]-methyl-carbamic acid tert-butyl ester (A); [5-(5-Ethoxymethoxy-benzofuran-2-yl)-6-nitro-pyridin-2-yl]-methyl-carbamic acid tert-butyl ester (B); Sodium sulphate (C); and Sodium chloride (D). Vertical axis represents intensity (counts) and horizontal axis represents position (°2theta for Cu Kα-radiation).

One embodiment relates to the compound [6-(5-Ethoxymethoxy-benzofuran-2-yl)-2-nitro-pyridin-3-yl]-methyl-carbamic acid tert-butyl ester as described in FIG. 1. Another embodiment relates to the compound [5-(5-Ethoxymethoxy-benzofuran-2-yl)-6-nitro-pyridin-2-yl]-methyl-carbamic acid tert-butyl ester as described in FIG. 3.

As used herein, "pharmaceutically acceptable" is employed to refer to those compounds and/or materials, compositions, and/or dosage forms which are, within the scope of sound medical judgment, suitable for use in contact with the tissues of mammals without excessive toxicity, irritation, allergic response, or other problem or complication and commensurate with a reasonable benefit/risk ratio.

As used herein, "a free base or a pharmaceutically acceptable salt" refer to ansolvates, including anhydrates and desolvated solvates, and solvates, including hydrates. As used herein, "pharmaceutically acceptable salts" refer to derivatives of the disclosed compounds wherein the parent compound is modified by making acid or base salts or cocrystals thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, phosphoric, and the like; and the salts prepared from organic acids such as lactic, maleic, citric, benzoic, methanesulfonic, and the like.

The pharmaceutically acceptable salts of the compounds of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used.

An "isotopically-labeled", "radio-labeled", "labeled", "detectable" or "detectable amyloid binding" compound or agent, or a "radioligand" is a compound where one or more atoms are replaced or substituted by an atom having an atomic mass or mass number different from the atomic mass or mass number typically found in nature (i.e., naturally occurring). One non-limiting exception is $^{19}F$, which allows detection of a molecule which contains this element without enrichment to a higher degree than what is naturally occurring. Compounds carrying the substituent $^{19}F$ may thus also be referred to as "labeled" or the like. Suitable radionuclides (i.e. "detectable isotopes") that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. It is to be understood that an isotopically labeled compound needs only to be enriched with a detectable isotope to, or above, the degree which allows detection with a technique suitable for the particular application, e.g. in a detectable compound labeled with $^{11}C$, the carbon-atom of the labeled group of the labeled compound may be constituted by $^{12}C$ or other carbon-isotopes in a fraction of the molecules. The radionuclide that is incorporated in the radiolabeled compounds will depend on the specific application of that radiolabeled compound. For example, for in vitro plaque or receptor labelling and in competition assays, compounds that incorporate $^{3}H$, $^{14}C$, or $^{125}I$ will generally be most useful. For in vivo imaging applications $^{11}C$, $^{13}C$, $^{18}F$, $^{19}F$, $^{120}I$, $^{123}I$, $^{131}I$, $^{75}Br$, or $^{76}Br$ will generally be most useful.

Examples of an "effective amount" include amounts that enable imaging of amyloid deposit(s) in vivo at bioavailability levels for pharmaceutical or imaging use, and/or prevent cell degeneration and toxicity associated with fibril formation.

The compounds of the present invention may be used as precursor for a radioligand or as a radioligand, to determine the presence, location and/or amount of one or more amyloid deposit(s) in an organ or body area, including the brain, of an animal or human. Amyloid deposit(s) include, without limitation, deposit(s) of Aβ (amyloid beta). In allowing the temporal sequence of amyloid deposition to be followed, the inventive compounds, as precursor for a radioligand or as a radioligand, may further be used to correlate amyloid deposition with the onset of clinical symptoms associated with a disease, disorder or condition. The inventive compounds may ultimately be used to treat, and to diagnose a disease, disorder or condition characterized by amyloid deposition, such as AD, familial AD, Down's syndrome, amyloidosis and homozygotes for the apolipoprotein E4 allele.

The compounds of the invention, as precursor for a radioligand or as a radioligand, can thus be used in an in vivo method for measuring amyloid deposits in a mammal, comprising the steps of: (a) administering a detectable quantity of a pharmaceutical composition as set out in the paragraph above, and (b): detecting the binding of the compound to amyloid deposit in the subject.

The method determines the presence and location of amyloid deposits in an organ or body area, preferably brain of a patient. The present method comprises administration of a detectable quantity of a pharmaceutical composition containing an amyloid-binding compound of the present invention called a "detectable compound," or a pharmaceutically acceptable water-soluble salt thereof, to a patient.

A "detectable quantity" means that the amount of the detectable compound that is administered is sufficient to enable detection of binding of the compound to amyloid. An "imaging effective quantity" means that the amount of the detectable compound that is administered is sufficient to enable imaging of binding of the compound to amyloid.

The invention employs amyloid probes which, in conjunction with non-invasive neuroimaging techniques such as magnetic resonance spectroscopy (MRS) or imaging (MINI), or gamma imaging such as positron emission tomography (PET) or single-photon emission computed tomography (SPECT), are used to quantify amyloid deposition in vivo. The term "in vivo imaging", or "imaging", refers to any method which permits the detection of a labelled heteroaryl substituted benzofuran or benzothiophene derivatives as described herein. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. A "subject" is a mammal, preferably a human, and most preferably a human suspected of having dementia.

For purposes of in vivo imaging, the type of detection instrument available is a major factor in selecting a given label. For instance, radioactive isotopes and $^{19}F$ are particularly suitable for in vivo imaging. The type of instrument used will guide the selection of the radionuclide or stable isotope. For instance, the radionuclide chosen must have a type of decay detectable by a given type of instrument.

Another consideration relates to the half-life of the radionuclide. The half-life should be long enough so that it is still detectable at the time of maximum uptake by the target, but short enough so that the host does not sustain deleterious radiation. The radiolabeled compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range.

For PET detection, the radiolabel will be a positron-emitting radionuclide, such as $^{18}F$ or $^{11}C$, which will annihilate to form two gamma rays, which will be detected by the PET camera.

In the present invention, precursors for amyloid binding compounds/probes are made and these compounds/probes are useful for in vivo imaging and quantification of amyloid deposition. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the 2-heteroaryl substituted benzofuran derivatives may be labeled with $^{19}F$ or $^{13}C$ for MRS/MRI by general organic chemistry techniques known in the art. The compounds may also be radiolabeled with, for example, $^{18}F$, $^{11}C$, $^{75}Br$, $^{76}Br$, or $^{120}I$ for PET by techniques well known in the art such as described by Fowler, J. and Wolf, A. in "Positron Emission Tomography and Autoradiography" 391-450 (Raven Press, 1986). The compounds may also be radiolabeled with $^{123}I$ and $^{131}I$ for SPECT by any of several techniques known to the art. See, e.g., Kulkarni, Int. J. Rad. Appl. & Inst. (Part B) 18: 647 (1991). The compounds may also be radiolabeled with known metal radiolabels, such as Technetium-99m ($^{99m}Tc$). The metal radiolabeled compound can be used to detect amyloid deposits. Preparing radiolabeled derivatives of Tc-99m is well known in the art. See, for example, Zhuang et al. Nuclear Medicine & Biology 26(2): 217-24, (1999); Oya et al. Nuclear Medicine &Biology 25(2): 135-40, (1998), and Hom et al. Nuclear Medicine &Biology 24(6):485-98, (1997). In addition, the compounds may be labeled with $^3$H, $^{14}$C and $^{125}$I, by methods well known to the one skilled in the art, for detection of amyloid plaque in vitro and post mortem samples. Furthermore, fluorescent compounds may be used for the detection of plaques present in vitro and post mortem samples by employment of well-known techniques based on the detection of fluorescence.

Elements particularly useful in magnetic resonance spectroscopy include $^{19}$F and $^{13}$C. Suitable radioisotopes for purposes of this invention include beta-emitters, gamma-emitters, positron-emitters and x-ray emitters. These radioisotopes include $^{120}$I, $^{123}$I, $^{131}$I, $^{125}$I, $^{18}$F, $^{11}$C, $^{75}$Br, and $^{76}$Br. Suitable stable isotopes for use in Magnetic Resonance Imaging (MRI) or Spectroscopy (MRS), according to this invention, include $^{19}$F and $^{13}$C. Suitable radioisotopes for in vitro quantification of amyloid in homogenates of biopsy or post-mortem tissue include $^{125}$I, $^{14}$C, and $^3$H. The preferred radiolabels are $^{11}$C and $^{18}$F for use in PET in vivo imaging, $^{123}$I for use in SPECT imaging, $^{19}$F for MRS/MRI, and $^3$H and $^{14}$C for in vitro studies. However, any conventional method for visualizing diagnostic probes can be utilized in accordance with this invention.

The radiolabeled, final compounds deriving from the compounds of the present invention may be administered by any means known to one of ordinary skill in the art. For example, administration to the animal may be local or systemic and accomplished orally, parenterally, by inhalation spray, topically, rectally, inhaled, nasally, buccally, vaginally, or via an implanted reservoir. The term "parenteral" as used herein includes subcutaneous, intravenous, intraarterial, intramuscular, intraperitoneal, intrathecal, intraventricular, intrasternal, intracranial, and intraosseous injection and infusion techniques.

Dose levels can range from about 0.001 μg/kg/day to about 10,000 mg/kg/day. In one embodiment, the dose level is about 0.001 μg/kg/day to about 10 g/kg/day. In another embodiment, the dose level is about 0.01 μg/kg/day to about 1.0 g/kg/day. In yet another embodiment, the dose level is about 0.1 mg/kg/day to about 100 mg/kg/day.

The exact administration protocol and dose levels will vary depending upon various factors including the age, body weight, general health, sex and diet of the patient; the determination of specific administration procedures would be routine to any one of ordinary skill in the art.

The regimen may include pre-treatment and/or co-administration with additional compounds such as for example therapeutic agent(s).

Process for Preparing the Compounds of the Invention.

Scheme 1. Synthesis of 5-ethoxymethoxy-benzofuran-2-boronic acid (4)

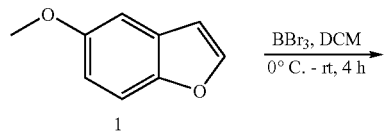

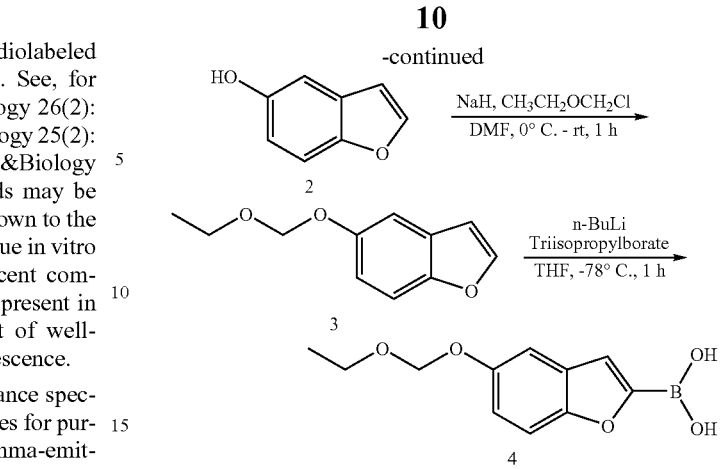

One embodiment of the invention relates to a process for making 5-ethoxymethoxy-benzofuran-2-boronic acid, wherein the process comprises:
converting compound 1 into compound 2 with a deprotection reagent in a solvent;
converting compound 2 into compound 3 with a base and a protection reagent in a solvent; and
converting compound 3 into 5-ethoxymethoxy-benzofuran-2-boronic acid by a process comprising deprotonating compound 3 with a base and mixing the deprotonated product with a trialkylborate in a solvent, wherein;

compound 1 corresponds to:

compound 2 corresponds to:

; and compound 3 corresponds to:

.

The end product of the different reaction steps may be further purified or recrystallised if needed.

Suitable solvents for step a) are for example, but not limited to, chlorinated solvents such as dichloromethane, aromatic solvent, such as toluene, amides such as dimethylformamide and N-methylpyrrolidone and alkanes such as hexane and heptane, or mixtures thereof.

Suitable solvents for step b) are for example, but not limited to, chlorinated solvents such as dichloromethane, aromatic solvents such as toluene, amides such as dimethylformamide and N-methylpyrrolidone, ethers such as tetrahydrofuran, 2-methyltetrahydrofuran, tert-butylmethylether, cyclopentyl methyl ether and diethyl ether, and alkanes such as hexane and heptane, or mixtures thereof.

Suitable solvents for step c) are for example, but not limited to, aromatic solvents such as toluene and xylene, ethers such as tetrahydrofuran, 2-methyltetrahydrofuran, tert-butylmethylether, cyclopentyl methyl ether and diethyl ether, and alkanes such as hexane and heptane, or mixtures thereof.

In one embodiment the solvent used in step a) is dichloromethane, toluene or N-methylpyrrolidone.

In another embodiment the solvent used in step b) is cyclopentyl methyl ether, tetrahydrofuran or 2-methyl tetrahydrofuran.

In a further embodiment the solvent used in step c) is hexane, tetrahydrofuran or 2-methyl tetrahydrofuran.

The total amount of solvents used in steps a-c may vary in the range of from about 2-100 (v/w) volume per weight of starting material, particularly in the range of 6-20 (v/w) volume per weight of starting material.

Suitable reagents for step a) are for example, but not limited to, Lewis acids such as $BBr_3$ and $BCl_3$, alkylthiolates such as sodium thiomethylate and sodium thiooctylate and pyridine hydrochloride.

Suitable reagents for step b) are for example, but not limited to, ethoxy methoxyhalides such as ethoxy methoxy bromide or ethoxy methoxy chloride and metal hydrides such as sodium hydride or litium hydride.

Suitable reagents for step c) are for example, but not limited to, alkyllitium reagents such as methyllitium, butyllitium and hexyllitium and trialkylborates such as trimethylborate, tripropylborate, triisopropylborate and tributylborate.

In one embodiment the reagents used in step a) are BBr3 or pyridine hydrochloride In another embodiment the reagents used in step b) is ethoxy methoxy chloride with sodium hydride or litium hydride.

In a further embodiment the reagents used in step c) are bultyllitium and triisopropylborate.

In one embodiment the reagent in step a) is boron tribromide.

In another embodiment the reagent in step a) is pyridine hydrochloride.

In another embodiment the reagents in step b) are sodium hydride in mixture with chloromethyl ethyl ether.

In another embodiment the reagents in step b) are Lithium hydride in mixture with chloromethyl ethyl ether.

In another embodiment the reagents in step c) are n-butyllithium in mixture with triisopropylborate.

Another embodiment relates to the process described above in scheme 1 wherein the process comprises:

converting compound 1 into compound 2 using $BBr_3$ in dichloromethane;

converting compound 2 into compound 3 using NaH and $CH_3CH_2OCH_2Cl$ in dimethylformamide; and converting compound 3 into 5-ethoxymethoxy-benzofuran-2-boronic acid by a process comprising deprotonating compound 3 using n-butyllithium and mixing the deprotonated product with triisopropylborate in tetrahydrofuran.

The temperature for steps a-c may be in the range of from about −78-250° C., particularly in the range of about from −25-200° C.

Scheme 2. Synthesis of [6-(5-ethoxymethoxy-benzofuran-2-yl)-2-nitro-pyridin-3-yl]-methyl-carbamic acid tert-butyl ester (8)

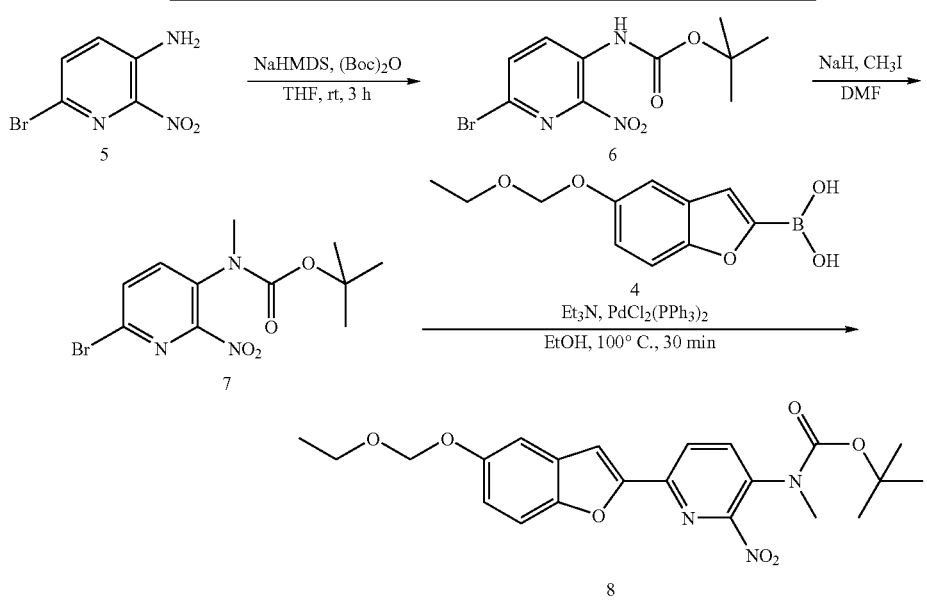

One embodiment of the invention relates to a process for making [6-(5-ethoxymethoxy-benzofuran-2-yl)-2-nitro-pyridin-3-yl]-methyl-carbamic acid tert-butyl ester, wherein the process comprises:

converting compound 5 into compound 6 by a process comprising protecting the amino group in compound 5 using a protecting group in the presence of a base;

converting compound 6 into compound 7 by a process comprising alkylating compound 6 using an alkylating agent in the presence of a base; and reacting compound 7 and compound 4 in the presence of a palladium catalyst and base in a solvent; wherein;

compound 4 corresponds to:

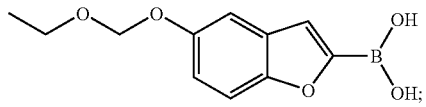

compound 5 corresponds to:

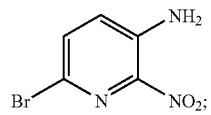

compound 6 corresponds to:

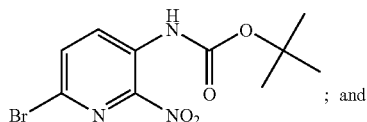

; and compound 7 corresponds to:

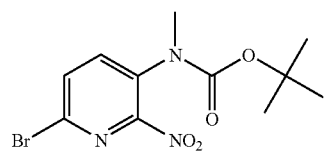

.

The end product of the different reaction steps may be further purified or recrystallised if needed.

Suitable solvents are for example, but not limited to, in step d) THF or diethylether; in step e) DMF or THF; in step f) ethanol or DMF, or mixtures thereof.

In one embodiment the solvent in step d) is THF.

In another embodiment the solvent in step e) is DMF.

In a further embodiment the solvent in step f) is ethanol.

Suitable bases are for example, but not limited to, in step d) NaHMDS, KHMDS, or NaH, in step e) NaH, NaHMDS; in step f) $Et_3$-N or $K_2CO_3$.

In another embodiment the base in step d) is NaHMDS.

In one embodiment the base in step e) is NaH.

In a further embodiment the base in step f) is $Et_3$-N.

Suitable catalysts for step f) are for example but not limited to, Pd(PPh3)$_2$Cl$_2$ or Pd(dppf)Cl$_2$ Another embodiment relates to the process described above in scheme 2 wherein the process comprises:

converting compound 5 into compound 6 by a process comprising protecting the amino group in compound 5 using t-butyl dicarbonate in the presence of sodium hexamethyldisilazide;

converting compound 6 into compound 7 by a process comprising alkylating compound 6 using $CH_3I$ in the presence of NaH; and reacting compound 7 and compound 4 in the presence of dichlorobis(triphenylphosphine)palladium(II) and $(CH_3CH_2)_3N$ in ethanol.

The reaction temperatures for steps d-f are between −80 to room temperature.

Scheme 3. Synthesis of (5-Bromo-6-nitro-pyridin-2-yl)-methyl-carbamic acid tert-butyl ester (12)

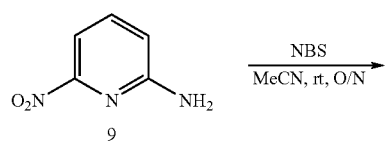

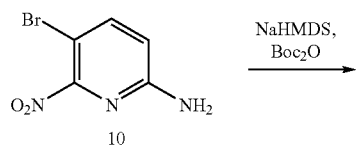

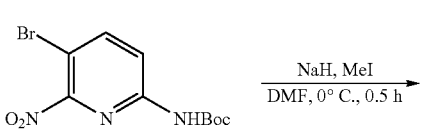

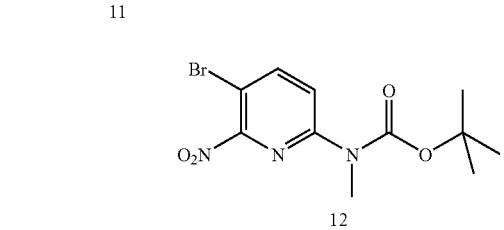

One embodiment of the invention relates to a process for making (5-Bromo-6-nitro-pyridin-2-yl)-methyl-carbamic acid tert-butyl ester, wherein the process comprises:

converting compound 9 into compound 10 by a process comprising bromination of compound 9 in a solvent using a bromination reagent;

converting compound 10 into compound 11 by a process comprising combining compound 10 and compound 11 in a solvent in the presence of a base followed by addition of t-butyl dicarbonate; and converting compound 11 into (5-bromo-6-nitro-pyridin-2-yl)-methyl-carbamic acid tert-butyl ester by a process comprising alkylating compound 11 in a solvent using an alkylating agent the presence of a base; wherein;

compound 9 corresponds to:

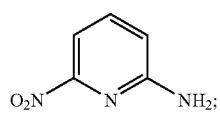

compound 10 corresponds to:

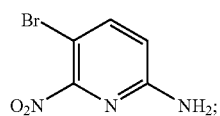

compound 11 corresponds to:

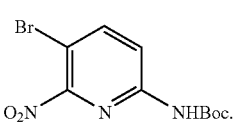

The end product of the different reaction steps may be further purified or recrystallised if needed.

Suitable solvents for step g-i are for example, but not limited to, nitriles such as acetonitrile and propionitrile, chlorinated solvents such as dichloromethane, aromatic solvents such as toluene and xylene, ethers such as tetrahydrofuran, 2-methyltetrahydrofuran, tert-butylmethylether, cyclopentyl methyl ether and diethyl ether, amides such as dimethylformamide and N-methylpyrrolidone and alkanes such as hexane and heptane, or mixtures thereof.

In one embodiment the solvent used in step g) is water, acetonitrile (MeCN), toluene, tetrahydrofuran, or mixtures thereof.

In another embodiment the solvent used in step h) is tetrahydrofuran, heptane, 2-methyl tetrahydrofuran, or mixtures thereof.

In a further embodiment solvent used in step i) is water, hexane, acetonitrile, dimethyl formamide, tetrahydrofurane, 2-methyl tetrahydrofurane, or mixtures thereof.

In one embodiment the solvent in step g) is MeCN mixed with water.

In another embodiment the solvent in step h) is THF mixed with heptane.

In another embodiment the solvent in step h) is THF mixed with hexane.

In a further embodiment the solvent in step i) is DMF mixed with water.

In another embodiment the solvent in step i) is THF mixed with heptane.

In a further embodiment the solvent in step i) is MeCN mixed with water.

The total amount of solvents used in steps g) to i may vary in the range of from about 2-100 (v/w) volume per weight of starting material, particularly in the range of 6-20 (v/w) volume per weight of starting material.

Suitable reagents for step g) are for example, but not limited to bromination reagents such as N-bromosuccinimide.

Suitable reagents for step h) are for example, but not limited to, di-tert-butyl dicarbonate and base such as sodium bis(trimethylsilyl)amide, sodium hydride or litium hydride.

In one embodiment the reagents used in step h) are di-tert-butyl dicarbonate with sodium hydride, litium hydride or sodium bis(trimethylsilyl)amide.

Suitable reagents for step i) are for example, but not limited to, alkylation reagents such as methyl iodide and dimethylsulphate, and base such as sodium hydride, litium hydride, sodium bis(trimethylsilyl)amide and 1,8-Diazabicyclo[5.4.0]undec-7-ene.

In another embodiment the reagent in step g) is N-bromosuccinimide.

In one embodiment the base in step h) is NaHMDS and Boc₂O.

In a further embodiment the base in step i) is DBU.
In a further embodiment the base in step i) is NaH.

Another embodiment relates to the process described above in scheme 3 wherein the process comprises:
converting compound 9 into compound 10 by a process comprising bromination of compound 9 in CH₃CN using n-bromosuccinimide;
converting compound 10 into compound 11 by a process comprising combining compound 10 and compound 11 in a solvent in the presence of sodium hexamethyldisilazide followed by addition of t-butyl dicarbonate; and
converting compound 11 into (5-bromo-6-nitro-pyridin-2-yl)-methyl-carbamic acid tert-butyl ester by a process comprising alkylating compound 11 in dimethylformamide using CH₃I in the presence of NaH.

The temperature for steps g-i may be in the range of from about −78-150° C., particularly in the in the range of from about 0° to 50° C.

The product in step i), (5-Bromo-6-nitro-pyridin-2-yl)-methyl-carbamic acid tert-butyl ester (12) may be purified by precipitation from a DMF/water mixture or from a MeCN/water mixture.

In one embodiment the (5-Bromo-6-nitro-pyridin-2-yl)-methyl-carbamic acid tert-butyl ester (12) is purified from a MeCN/water mixture.

Scheme 4. Alternative routes to (5-Bromo-6-nitro-pyridin-2-yl)-methyl-carbamic acid tert-butyl ester (12):

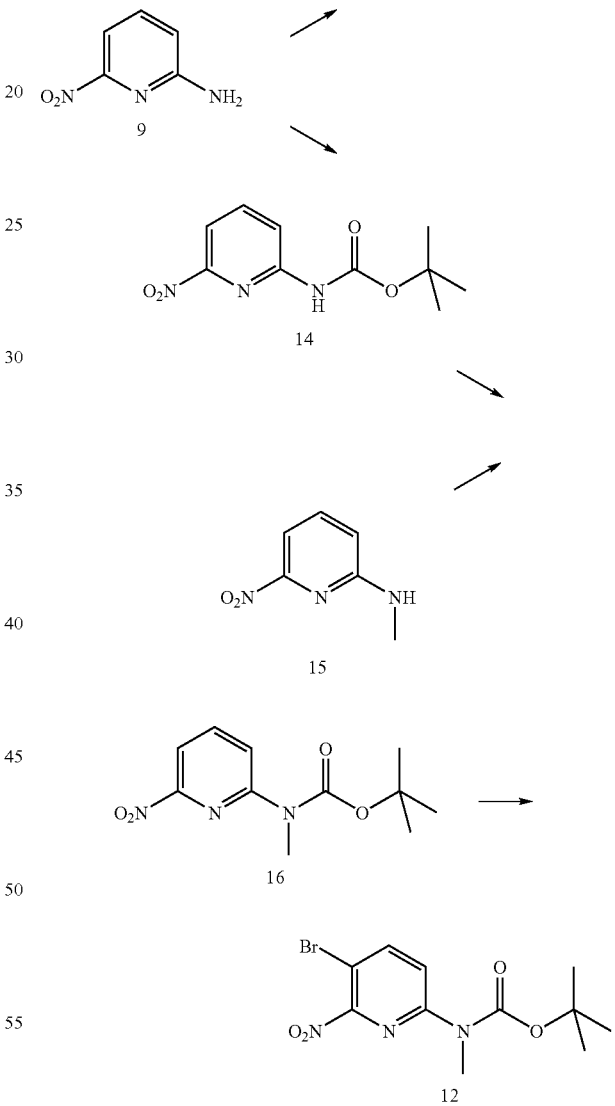

The (5-Bromo-6-nitro-pyridin-2-yl)-methyl-carbamic acid tert-butyl ester (12) could be prepared by two alternative routes. For example compound 12 can be prepared from 6-nitro-pyridin-2-ylamine (9), either via the N-methyl-6-nitropyridin-2-amine (14) or tert-butyl methyl (6-nitropyridin-2-yl)carbamate (16), where the bromination is introduced last in both sequences Scheme 4. Synthesis of [5-(5-ethoxymethoxy-benzofuran-2-yl)-6-nitro-pyridin-2-yl]-methyl-carbamic acid tert-butyl ester (13)

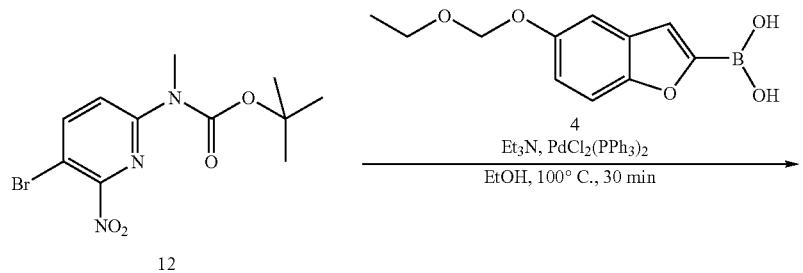

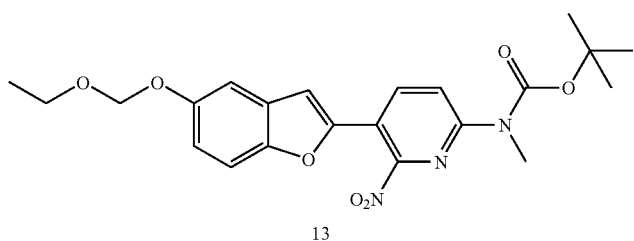

One embodiment of the invention relates to a process for the preparation of compound 13 by mixing compound 12 and compound 4 in a suitable solvent using a suitable base in the presence of a suitable catalyst followed by extraction.

The end product may be further purified or recrystallised if needed.

Suitable solvents are for example, but not limited to, alcohols such as methanol, ethanol, propanol, isopropanol and butanol, ethers such as dioxane, tetrahydrofuran and 2-methyltetrahydrofuran and aromatic solvents such as benzene, toluene and xylene, or mixtures thereof.

In one embodiment the solvent in step j) is ethanol.

The total amount of solvents used in step j) may vary in the range of from about 2-100 (v/w) volume per weight of starting material, particularly in the range of 6-20 (v/w) volume per weight of starting material.

Suitable reagents are for example, but not limited to, amines, such as triethylamine, carbonates such as cesium carbonate, potassium carbonate and sodium carbonate, phosphates such as potassium phosphate and sodium phosphate or potassium fluoride together with palladium catalysts. Also, a plethora of suitable phosphine ligands and imidazol-2-ylidene ligands may be considered.

In another embodiment the reagents in step j) are triethylamine and $PdCl_2(PPh_3)_2$.

The temperature for step j) may be in the range of from about -0° C. to 150° C., particularly in the in the range of from about 25° C. to 100° C.

Scheme 5. Alternative synthesis of [5-(5-Ethoxymethoxy-benzofuran-2-yl)-6-nitro-pyridin-2-yl]-methyl-carbamic acid tert-butyl ester (13) via direct arylation.

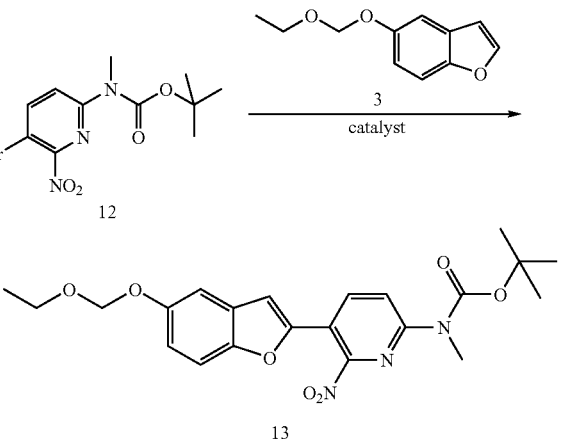

The [5-(5-Ethoxymethoxy-benzofuran-2-yl)-6-nitro-pyridin-2-yl]-methyl-carbamic acid tert-butyl ester (13) could be manufactured via a direct arylation of 5-ethoxymethoxy-benzofuran (3) with (5-bromo-6-nitro-pyridin-2-yl)-methyl-carbamic acid tert-butyl ester (12) in the presence of a suitable catalyst.

Suitable solvents are for example, but not limited to, amides such as dimethylacetamide, aromatic solvents such as toluene, and xylene The total amount of solvents used in steps g to i may vary in the range of from about 2-100 (v/w) volume per weight of starting material, particularly in the range of 6-20 (v/w) volume per weight of starting material.

Suitable reagents are for example, but not limited to, palladium catalyst systems such as $Pd(PPh_3)_4$ with potassium acetate or palladium acetate with tricyclohexylphosphine, pivaloylalcohol and potassium carbonate.

COMPOUND EXAMPLES

Below follows a number of non-limiting examples of precursor compounds of the invention.

General Methods

All solvents used were commercially available and were used without further purification. Reactions were typically run using anhydrous solvents under an inert atmosphere of nitrogen.

$^1H$ and $^{13}C$ NMR spectra were recorded at 400 MHz for proton and 100 MHz for carbon-13 on a Varian Mercury Plus 400 NMR Spectrometer equipped with a Varian 400 ATB PFG probe. All deuterated solvents contained typically 0.03% to 0.05% v/v tetramethylsilane, which was used as the reference signal (set at δ 0.00 for both $^1H$ and $^{13}C$).

Mass spectra were recorded on a Waters MS consisting of an Alliance 2795 (LC) and Waters Micromass ZQ detector at 120° C. The mass spectrometer was equipped with an electrospray ion source (ES) operated in a positive or negative ion mode. The mass spectrometer was scanned between m/z 100-1000 with a scan time of 0.3 s.

HPLC analyses were performed on a Water 600 Controller system with a Waters 717 Plus Autosampler and a Waters 2996 Photodiiode Array Detector. The column used was an ACE $C_{18}$, 5 μm, 4 60×150 mm. In a 20 min run, a linear gradient was applied starting from 95% A (A: 0.1% $H_3PO_4$ in water) and ending at 90% C(C:MeCN) over 6 min, holding at 90% C for 4 min and then ending back at 95% A. The column was at ambient temperature with the flow rate of 1.0 mL/min. The Diode Array Detector was scanned from 200-400 nm.

Microwave heating was performed either on a CEM Discover LabMate or on a Biotage Initiator System at the indicated temperature in the recommended microwave tubes.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), vanillin (generated by dissolving about 1 g vanillin in 100 mL 10% $H_2SO_4$), ninhydrin (available commercially from Aldrich), or Magic Stain (generated by thoroughly mixing 25 g $(NH_4)_6Mo_7O_{24} \cdot 4H_2O$, 5 g $(NH_4)_2Ce(IV)(NO_3)_6$, 450 mL $H_2O$ and 50 mL concentrated $H_2SO_4$) to visualize the compound. Flash chromatography was preformed using 40-63 μm (230-400 mesh) silica gel from Silicycle following analogous techniques to those disclosed in Still, W. C.; Kahn, M.; and Mitra, M. *Journal of Organic Chemistry*, 1978, 43, 2923-2925. Typical solvents used for flash chromatography or thin layer chromatography were mixtures of dichloromethane/methanol, ethyl acetate/methanol and hexanes/ethyl acetate.

Preparative chromatography was performed on either a Waters Prep LC 4000 System using a Waters 2487 Diode Array or on a Waters LC Module 1 plus. The column used was either a Waters XTerra Prep $C_{18}$, 5 μm, 30×100 mm (flow rate 40 mL/min) or a Phenomenex Luna $C_{18}$, 5 μm, 21.6×250 mm (flow rate 20 mL/min). Narrow gradients with acetonitrile/water, with the water containing either 0.1% trifluoroacetic acid or 10 mM ammonium acetate, were used to elute the compound in a total run time between 20-30 min.

X-Ray Powder Diffraction (XRPD) patterns were collected on a PANalytical X'Pert PRO MPD theta-theta system using long-fine-focus Cu Kα-radiation (40 kV, 50 mA) and an X'Celerator-detector. A programmable divergence slit and a programmable anti-scatter slit giving an irradiated length of 20 mm were used. 0.02 rad Soller slits were used on the incident and on the diffracted beam path. A 20 mm fixed mask was used on the incident beam path and a Nickel-filter was placed in front of the detector. Thin flat samples were prepared on flat silicon zero background plates using a spatula. The plates were mounted in sample holders and rotated in a horizontal position during measurement. Diffraction patterns were collected between 2°2theta and 80°2theta in a continuous scan mode. Total time for a scan was 25 minutes 30 seconds. The skilled person of X-ray powder diffraction will realise that the relative intensity of peaks can be affected by, for example, grains above approximately 30 micrometer in size and non-unitary aspect ratios, which may affect analysis of samples. Furthermore, it should be understood that intensities might fluctuate depending on experimental conditions and sample preparation such as preferred orientation of the particles in the sample. The use of automatic or fixed divergence slits will also influence the relative intensity calculations. A person skilled in the art can handle such effects when comparing diffraction patterns.

The skilled person will also realise that the position of reflections can be affected by the precise height at which the sample sits in the diffractometer, temperature and the zero calibration of the diffractometer. The surface planarity of the sample may also have a small effect. The exact value for the position of a reflection can vary slightly between samples, e.g. due to differences in crystallinity of the material. The use of automatic peak finding programs or manual, subjective, peak determination may also slightly affect the reported position of a reflection. It is obvious for the skilled person that differences in instrument performance can influence peak resolution. Hence the diffraction pattern data presented are not to be taken as absolute values.

Generally, a measurement error of a diffraction angle in an X-ray powder diffractogram is about 5% or less, in particular within the range plus 0.5° 2-theta to minus 0.5° 2-theta when using Cu Kα-radiation, and such degree of a measurement error should be taken into account when considering the X-ray powder diffraction patterns in FIGS. 1 to 5 and when reading Tables 1 and 2.

The skilled person will also realise that traces of any crystalline impurities from the preparation of the sample material, e.g. salt residues such as sodium sulphate or sodium chloride from drying, salting-out and/or pH-adjusting steps, might cause diffraction and that peaks having diffraction angles near expected peaks from such crystalline impurities might wholly or partially emanate from such crystalline impurities.

Diffraction patterns from many compounds can be simulated, e.g. from databases such as the Powder Diffraction File (PDF) databases from the International Centre for Diffraction Data (ICDD). The skilled person can compare such simulated diffraction patterns with experimental patterns.

Differential scanning calorimetry (DSC) from 30° C. to 300° C. was performed under nitrogen in aluminium sample cups with perforated lids using a Perkin Elmer Diamond DSC instrument. The scan rate was 10° C. per minute. The sample size was less than 1 mg. It is well known that the DSC onset and peak temperatures as well as energy values may vary due to, for example, the purity of the sample and sample size and due to instrumental parameters, especially the temperature scan rate. Hence the DSC data presented are not to be taken as absolute values.

A person skilled in the art can set up instrumental parameters for a Differential scanning calorimeter so that data comparable to the data presented here can be collected according to standard methods, for example those described in Höhne, G. W. H. et al (1996), Differential Scanning Calorimetry, Springer, Berlin.

Thermogravimetric analysis (TGA) from ambient temperature to 250° C. was performed under nitrogen in a platinum sample cup using a Perkin Elmer Pyris 1 TGA Thermogravimetric analyzer. The scan rate was 10° C. per minute. The sample size was less than 1 mg. It is well known that the TGA trace may vary due to, for example, the sample size and due to instrumental parameters, especially the temperature scan rate. Hence the TGA data presented are not to be taken as absolute values.

The following abbreviations have been used:
Ac acetyl;
aq. aqueous;
$Boc_2O$ di-tert-butyl dicarbonate;
DCM dichloromethane;
DIPEA N,N-Diisopropylethylamine;
DMF N,N-dimethylformamide;
DMSO dimethylsulfoxide;
DSC Differential Scanning Calorimetry
EtOH ethanol;
MeOH methanol;
HMDS bis(trimethylsilyl)amide;
NBS N-bromosuccinimide;
r.t. room temperature;
THF tetrahydrofuran;
TFA trifluoroacetic acid;
TGA Thermogravimetric Analysis
XRPD X-Ray Powder Diffraction
DBU 1,8-Diazabicyclo[5.4.0]undec-7-ene
$Et_3N$ Triethylamine Starting materials used were either available from commercial sources or prepared according to literature procedures and had experimental data in accordance with those reported.

Intermediate Example 1

5-ethoxymethoxy-benzofuran-2-boronic acid (4)

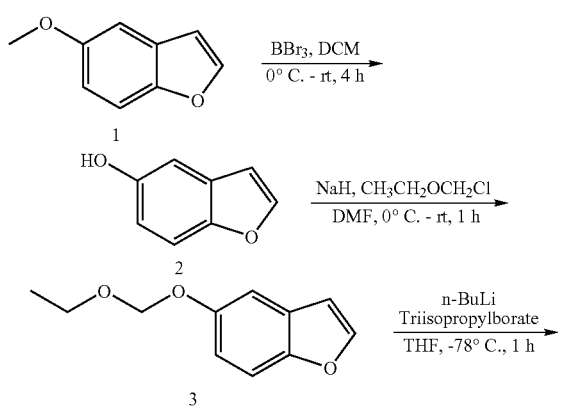

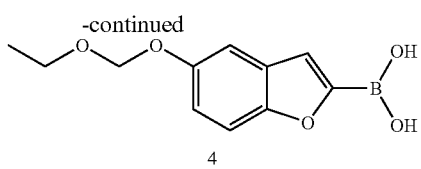

a) Benzofuran-5-ol (2)

To a stirred solution of 5-methoxybenzofuran (1) (0.50 g, 3.38 mmol) in dichloromethane (15 mL), boron tribromide (16.87 mL, 16.87 mmol, 1M solution in dichloromethane) was added slowly at 0° C. The reaction mixture was warmed to room temperature and stirred for 4 hours. The reaction mixture was then cooled to 0° C., quenched with aqueous saturated $NaHCO_3$ solution and extracted with dichloromethane (3×50 mL). The combined organic extracts were washed with brine (25 mL), dried over $Na_2SO_4$, and concentrated under reduced pressure to give compound (2) as an off white solid (300 mg) which was used in the next step without further purification.

$^1$H NMR (400 MHz, CHLOROFORM-d) δ: 7.59 (d, J=1.95 Hz, 1H), 7.35 (d, J=8.59 Hz, 1H), 7.00 (d, J=2.73 Hz, 1H), 6.80 (dd, 8.59, 2.74 Hz, 1H), 6.67 (m, 1H), 4.66 (s, 1H)

b) 5-Ethoxymethoxy-benzofuran (3)

To a stirred solution of benzofuran-5-ol (2) (257 mg, 1.92 mmol) in DMF (3 mL), NaH (81 mg, 1.92 mmol, 57% dispersion in oil) was added at 0° C. The reaction mixture was warmed to room temperature and stirred 1 hour. Chloromethyl ethyl ether (214 μL, 2.30 mmol) was then added drop wise to 0° C. and the mixture was stirred at room temperature for additional 1 hour. Water (10 mL) was added and the reaction mixture was extracted with ethyl acetate (2×50 mL). The organic extracts were washed with water, brine, dried over $Na_2SO_4$, and concentrated in vacuo. Purification of the crude product by flash column chromatography using 10% ethyl acetate in hexane afforded compound (3) (273 mg) as a colourless oil.

$^1$H NMR (400 MHz, CHLOROFORM-d) δ: 7.59 (d, J=1.95 Hz, 1H), 7.39 (d, J=8.16 Hz, 1H), 7.27 (d, J=2.73 Hz, 1H), 6.99 (dd, J=8.98, 2.34 Hz, 1H), 6.70 (m, 1H), 5.24 (s, 2H), 3.77 (q, J=7.03 Hz, 2H), 1.25 (t, J=7.03 Hz, 3H).

c) 5-Ethoxymethoxy-benzofuran-2-boronic acid (4)

To a stirred solution of 5-ethoxymethoxy-benzofuran (3) (265 mg, 1.38 mmol) in THF (5 mL) at −78° C., n-butyllithium (2.5M solution in hexane, 0.56 mL, 1.44 mmol) was added drop wise. After the reaction mixture was stirred for 1 hour, triisopropylborate (0.635 mL, 2.76 mmol) was added slowly and the stirring was continued for additional 20 minutes at −78° C. The reaction mixture was quenched with saturated ammonium chloride solution (10 mL) and was allowed to warm to room temperature. Water (10 mL) was added and the resulting mixture was extracted in diethyl ether (2×50 mL). The combined extracts were washed with brine, dried over $MgSO_4$, and concentrated under reduced pressure. Purification of the crude product by recrystallization from ethyl acetate and hexane afforded the desired compound (4) (170 mg) as a white solid.

$^1$H NMR (DMSO-$d_6$, 400 MHz) δ: 8.54 (s, 2H), 7.48 (d, J=8.6 Hz, 1H), 7.39 (s, 1H), 7.30 (d, J=2.7 Hz, 1H), 7.02 (dd, J=8.8, 2.5 Hz, 1H), 5.23 (s, 2H), 3.68 (q, J=7.0 Hz, 2H), 1.14 (t, J=7.0 Hz, 3H)

Final Precursor Example 1

Synthesis of [6-(5-Ethoxymethoxy-benzofuran-2-yl)-2-nitro-pyridin-3-yl]-methyl-carbamic acid tert-butyl ester (8)

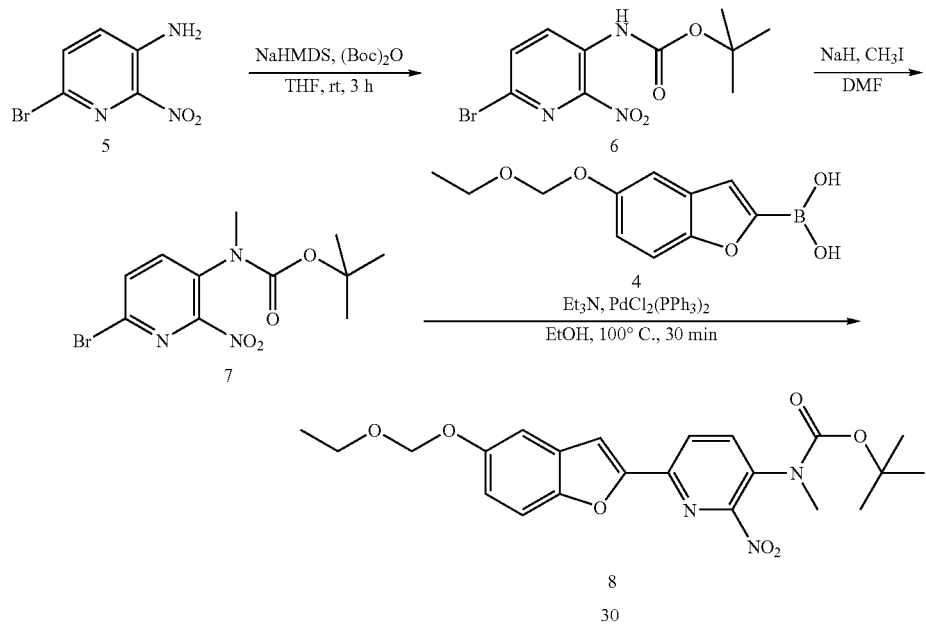

6-Bromo-2-nitro-pyridin-3-ylamine (5)

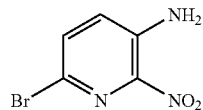

To a stirred suspension of 2-nitro-pyridin-3-ylamine (5.06 g, 36.40 mmol) and sodium acetate (2.99 g, 36.46 mmol) in acetic acid (40 mL), a solution of bromine (2.5 mL, 48.79 mmol) in acetic acid (8 ml) was added drop-wise and the reaction mixture was stirred overnight. The acetic acid was removed under reduced pressure. The residue was cooled to 0° C., neutralized with saturated sodium bicarbonate solution to adjust the pH to ~7, and extracted with ethyl acetate (4×50 mL). The combined organic extracts were washed with brine, dried over anhydrous $Na_2SO_4$, and concentrated under reduced pressure. The residue was triturated with ethyl acetate to afford compound (5) (5.1 g) as a yellow solid.

$^1$H NMR (DMSO-$d_6$, 400 MHz) δ: 7.66 (d, J=8.6 Hz, 1H), 7.58 (s, 2H), 7.49 (d, J=8.6 Hz, 1H)

ESMS: m/z 216.33 [M−1]$^-$ d) (6-Bromo-2-nitro-pyridin-3-yl)-carbamic acid tert-butyl ester (6)

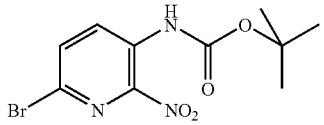

To a stirred solution of 6-bromo-2-nitro-pyridin-3-ylamine (5) (854 mg, 3.92 mmol) in THF (50 mL), NaHMDS (5.09 mL, 5.09 mmol, 1M in THF) was added at 0° C. After stirring for 15 minutes, a solution of di-tert-butyl dicarbonate (853 mg, 3.91 mmol) in THF (5 mL) was added over a period of 30 minutes. The reaction mixture was stirred for 3.5 hours at room temperature and then saturated aqueous $NaHCO_3$ was added. The reaction mixture was extracted with ethyl acetate (3×50 mL). The combined extracts were washed with water, brine, dried over $Na_2SO_4$, and concentrated under reduced pressure. The crude product was purified by flash column chromatography using 10% ethyl acetate in hexane to afford compound (6) (293 mg) as an off white solid.

$^1$H NMR (400 MHz, CHLOROFORM-d) δ: 9.41 (br. s., 1H), 9.00 (d, J=8.6 Hz, 1H), 7.73 (d, J=9.0 Hz, 1H), 1.55 ppm (s, 9H)

ESMS: m/z 318.36 [M+1]$^+$ e) (6-Bromo-2-nitro-pyridin-3-yl)-methyl-carbamic acid tert-butyl ester (7)

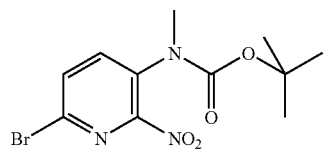

To a stirred solution of (6-bromo-2-nitro-pyridin-3-yl)-carbamic acid tert-butyl ester (6) (290 mg, 0.91 mmol) in DMF (10 mL), NaH (57 mg, 1.36 mmol, 57% dispersion in oil) was added at 0° C. After stirring for 15 minutes, methyl iodide (79 μL, 1.27 mmol) was added and the reaction mixture was stirred for 1 hour. The reaction mixture was then quenched with saturated ammonium chloride solution (15 mL) and extracted with ethyl acetate (2×40 mL). The combined organic extracts were washed with water, brine, dried over $MgSO_4$, and concentrated in vacuo. The residue was purified by flash column chromatography using 20% ethyl acetate in hexane to give compound (7) (268 mg) as a pale yellow solid.

¹H NMR (400 MHz, CHLOROFORM-d) δ: 7.78 (d, J=8.2 Hz, 1H), 7.66 (d, J=8.2 Hz, 1H), 3.29 (s, 3H), 1.39 (br. s., 9H)

ESMS: m/z 276.36 [M−56]⁻ f) [6-(5-Ethoxymethoxy-benzofuran-2-yl)-2-nitro-pyridin-3-yl]-methyl-carbamic acid tert-butyl ester (8)

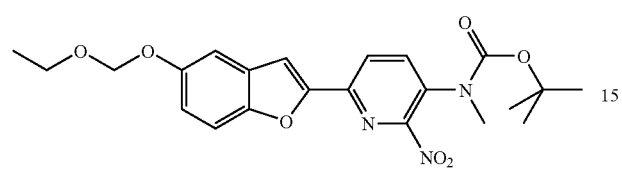

To a degassed solution of 5-ethoxymethoxy-benzofuran boronic acid (4) (140 mg, 0.593 mmol) in ethanol (10 mL), (6-bromo-2-nitro-pyridin-3-yl)-methyl-carbamic acid tert-butyl ester (7) (151 mg, 0.455 mmol), Pd(PPh₃)₂Cl₂ (42 mg, 0.059 mmol) and Et₃N (127 μL, 0.909 mmol) were added. The reaction mixture was stirred at 100° C. for 30 minutes in a microwave reactor. Volatiles were removed under reduced pressure. The residue was diluted with water (15 mL) and the mixture was extracted with ethyl acetate (3×50 mL). The combined organic extracts were washed with water, brine, dried over Na₂SO₄, and concentrated under reduced pressure. The crude product was purified by flash column chromatography using 20% ethyl acetate in hexane. Evaporation of solvent gave title compound 8 (170 mg) as a pale yellow solid.

¹H NMR (400 MHz, CHLOROFORM-d) δ: 8.10 (d, J=8.20 Hz, 1H), 7.84 (d, J=8.20 Hz, 1H), 7.50 (s, 1H), 7.45 (d, J=8.98 Hz, 1H), 7.32 (d, J=1.95 Hz, 1H), 7.02-7.16 (m, 1H), 5.27 (s, 2H), 3.78 (q, J=6.63 Hz, 2H), 3.32 (s, 3H), 1.36 (br. s., 9H), 1.26 (t, J=7.22 Hz, 3H)

ESMS: m/z 444.51 [M+1]⁺

DSC: endotherm event with onset at 109.5° C. and peak at 110.8° C. ΔH 89.6 Jg⁻¹

TGA: no marked events between room temperature and 160° C.

TABLE 1

Representative X-Ray Powder Diffraction peaks for [6-(5-Ethoxymethoxy-benzofuran-2-yl)-2-nitro-pyridin-3-yl]-methyl-carbamic acid tert-butyl ester

| Angle 2-Theta (2θ) Cu Kα | Relative Intensity |
| --- | --- |
| 6.97 | w |
| 9.24 | w |
| 11.27 | w |
| 12.00 | w |
| 13.51 | vs |
| 15.53 | s |
| 16.82 | s |
| 17.91 | w |
| 23.72 | s | vs = very strong
s = strong
w = weak

Intermediate example 2

(5-Bromo-6-nitro-pyridin-2-yl)-methyl-carbamic acid tert-butyl ester (12)

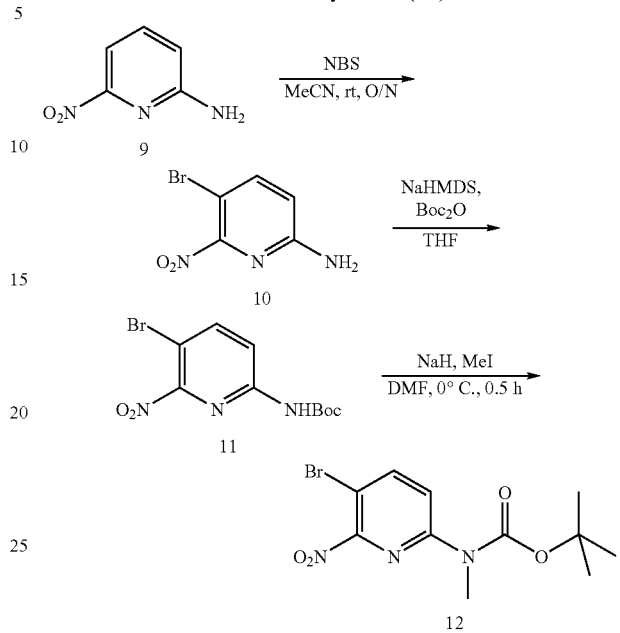

g) 5-Bromo-6-nitro-pyridin-2-ylamine (10)

To a stirred solution of 6-nitro-pyridin-2-ylamine (1.0 g, 7.18 mmol) in CH₃CN (100 mL), protected from light and under nitrogen atmosphere, N-bromosuccinamide (636 mg, 3.59 mmol) was added at 0° C. After 1 hour, another portion of N-bromosuccinamide (636 mg, 3.59 mmol) was added. The reaction mixture was allowed to warm to room temperature and stirring was continued overnight. The reaction mixture was then quenched by the addition of saturated aqueous Na₂S₂O₃ and extracted with ethyl acetate (3×30 mL). The combined organic extracts were washed with water, brine, dried over MgSO₄ (anhydrous) and concentrated in vacuo. The crude product was purified by Biotage using 10% ethyl acetate in hexane to afford 1.2 g of 5-bromo-6-nitro-pyridin-2-ylamine (10).

¹H NMR (400 MHz, DMSO-d₆) δ ppm: 7.84 (d, J=8.98 Hz, 1H), 7.03 (s, 2H), 6.66 (d, J=8.98 Hz, 1H)

h) (5-Bromo-6-nitro-pyridin-2-yl)-carbamic acid tert-butyl ester (11)

To a solution of 5-bromo-6-nitro-pyridin-2-ylamine (900 mg, 4.12 mmol) in dry THF (40 mL), NaHMDS (1M in THF, 5.8 mL) was added at 0° C. After stirring for 15 minutes, a solution of Boc₂O (901 mg, 4.12 mmol) in THF (5 mL) was added slowly at 0° C. over 30 minutes. The resulting mixture was warmed to room temperature, stirred for 3 hours, quenched with saturated aqueous NaHCO₃ and extracted with ethyl acetate (3×30 mL). The combined extracts were washed with water and brine, dried over Na₂SO₄ and concentrated under reduced pressure. The residue was purified by Biotage using 5-10% ethyl acetate in hexane to give 786 mg of (5-bromo-6-nitro-pyridin-2-yl)-carbamic acid tert-butyl ester (11).

¹H NMR (400 MHz, CHLOROFORM-d) δ ppm: 8.14 (d, J=8.98 Hz, 1H), 8.03 (d, J=8.59 Hz, 1H), 7.52 (s, 1H), 1.53 (s, 9H)

i) (5-Bromo-6-nitro-pyridin-2-yl)-methyl-carbamic acid tert-butyl ester (12)

To a solution of (5-bromo-6-nitro-pyridin-2-yl)-carbamic acid tert-butyl ester (11) (800 mg, 2.52 mmol) in dry DMF (15 mL), NaH (60% dispersion in mineral oil, 191 mg, 4.53 mmol) was added at 0° C. The resulting mixture was stirred for 30 minutes at 0° C. and methyl iodide (0.23 mL, 3.68 mmol) was then added. After stirring the reaction mixture for 30 minutes at 10° C., saturated aqueous NH$_4$Cl (15 mL) was added. The reaction mixture was extracted with ethyl acetate (3×30 mL). The combined extracts were washed with water, brine, dried over MgSO$_4$ (anhydrous) and concentrated under reduced pressure. The crude product was purified by Biotage using 10% ethyl acetate in hexane to afford (5-bromo-6-nitro-pyridin-2-yl)-methyl-carbamic acid tert-butyl ester 12 (789 mg).

$^1$H NMR (400 MHz, CHLOROFORM-d) δ ppm: 8.12 (d, J=8.60 Hz, 1H), 7.95 (d, J=8.99 Hz, 1H), 3.40 (s, 3H), 1.55 (s, 9H)

or alternative procedure for (5-Bromo-6-nitro-pyridin-2-yl)-methyl-carbamic acid tert-butyl ester (12):

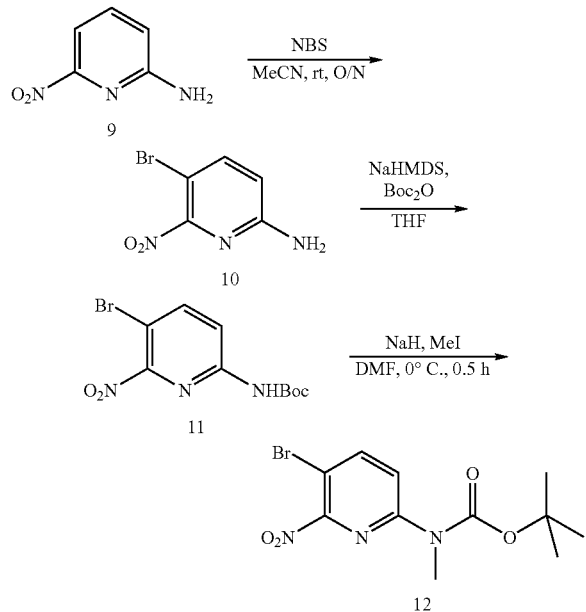

g) 5-Bromo-6-nitro-pyridin-2-ylamine (10)

To a stirred solution of 6-nitro-pyridin-2-ylamine (9) (5.1 g, 18.4 mmol) in MeCN (125 mL) under nitrogen atmosphere, N-bromosuccinimide (3.43 g, 19.3 mmol) was added at 0° C. After 1 hour, another portion of N-bromosuccinimide (3.57 g, 20.1 mmol) was added. The reaction mixture was allowed to warm to room temperature and stirring was continued overnight. The product was precipitated by addition of water (125 mL). The slurry was cooled to 0° C. and precipitated product was isolated by filtration, washed with premixed MeCN:water (1:1) and dried under vacuum at 40° C. to afford 3.8 g of 5-bromo-6-nitro-pyridin-2-ylamine (2).

$^1$H NMR (400 MHz, DMSO-d$_6$) δ ppm: 7.84 (d, J=8.98 Hz, 1H), 7.03 (s, 2H), 6.66 (d, J=8.98 Hz, 1H)

h) (5-Bromo-6-nitro-pyridin-2-yl)-carbamic acid tert-butyl ester (11)

To a solution of 5-bromo-6-nitro-pyridin-2-ylamine (10) (3.8 g, 18.4 mmol) in dry THF (40 mL), NaHMDS (1M in THF, 45 mL, 45 mmol) was added at 0° C. After stirring for 15 minutes, a solution of Boc$_2$O (28.3% wt in THF, 14.2 g, 18.4 mmol) was added slowly at 0° C. over 1 hour. The resulting mixture was quenched with aqueous NaHSO$_4$ (1 M, 110 mL, 110 mmol) and warmed to room temperature. The aqueous phase was discarded and the product containing organic phase was concentrated under reduced pressure. The residue was dissolved in THF (40 mL) and impurities were precipitated upon addition of heptane (160 mL) and removed by filtration. The clear-filtered product containing solution was evaporated to dryness yielding 4.2 g (5-bromo-6-nitro-pyridin-2-yl)-carbamic acid tert-butyl ester (11) as a dark, red-brown residue, which was used without further purification in the next step.

$^1$H NMR (400 MHz, CHLOROFORM-d) δ ppm: 8.14 (d, J=8.98 Hz, 1H), 8.03 (d, J=8.59 Hz, 1H), 7.52 (s, 1H), 1.53 (s, 9H)

i) (5-Bromo-6-nitro-pyridin-2-yl)-methyl-carbamic acid tert-butyl ester (12)

To a solution of (5-bromo-6-nitro-pyridin-2-yl)-carbamic acid tert-butyl ester (11) (4.2 g, 13.2 mmol) in dry DMF (21 mL), DBU (5.02 g, 33.0 mmol)! was added at 0° C. Methyl iodide (3.75 g, 26.4 mmol) was added slowly at 0° C. After stirring for 3 hours at 0° C. the reaction mixture was quenched and the product was precipitated upon addition of aqueous NaHSO$_4$ (1M). The crude product was isolated by filtration and purified by recrystallisation from a mixture of MeCN and water to afford (5-bromo-6-nitro-pyridin-2-yl)-methyl-carbamic acid tert-butyl ester 12 (1.55 g).

$^1$H NMR (400 MHz, CHLOROFORM-d) δ ppm: 8.12 (d, J=8.60 Hz, 1H), 7.95 (d, J=8.99 Hz, 1H), 3.40 (s, 3H), 1.55 (s, 9H)

Final Precursor Example 2

Synthesis of [5-(5-Ethoxymethoxy-benzofuran-2-yl)-6-nitro-pyridin-2-yl]-methyl-carbamic acid tert-butyl ester (13)

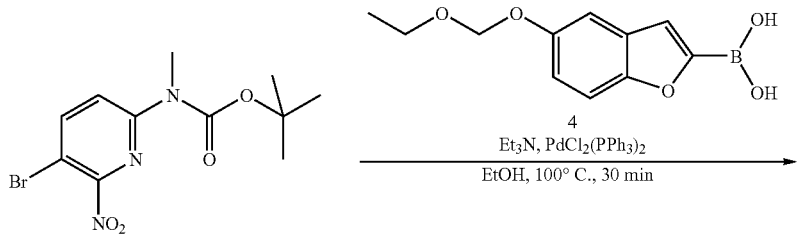

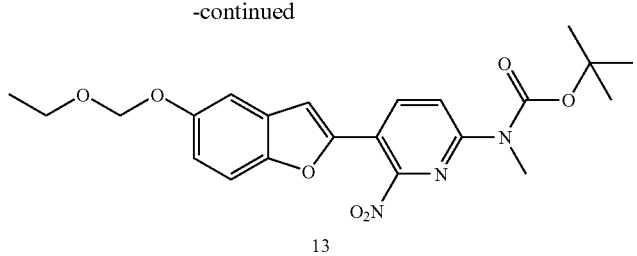

13 j) [5-(5-Ethoxymethoxy-benzofuran-2-yl)-6-nitro-pyridin-2-yl]-methyl-carbamic acid tert-butyl ester (13)

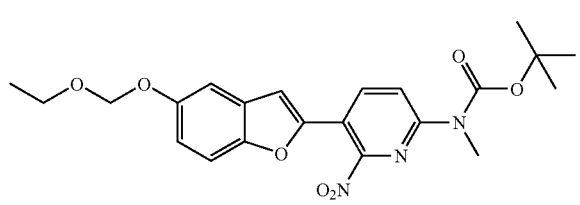

By following the same procedure as described in Example 1 (step d), was prepared using (5-bromo-6-nitro-pyridin-2-yl)-methyl-carbamic acid tert-butyl ester (12) (100 mg, 0.30 mmol) and 5-ethoxymethoxy-benzofuran-2-boronic acid (4) (92.5 mg, 0.39 mmol). Work-up as described in example 1d, followed by purification of the crude product by flash column chromatography using 10-25% ethyl acetate in hexane. Evaporation of solvent afforded 120 mg of the desired compound (13) as yellowish solid.

$^1$H NMR (400 MHz, acetone) δ ppm: 8.48 (d, J=8.59 Hz, 1H), 8.36 (d, J=8.98 Hz, 1H), 7.48 (d, J=8.98 Hz, 1H), 7.37 (d, J=2.73 Hz, 1H), 7.23 (s, 1H), 7.09 (dd, J=8.98, 2.34 Hz, 1H), 5.28 (s, 2H), 3.74 (q, J=7.02 Hz, 2H), 3.43 (s, 3H), 1.58 (s, 9H), 1.19 (t, J=7.02 Hz, 3H)

ESMS: m/z 444.44 [M+1]$^+$; 388.45 [(M−56)+1]$^+$

DSC: endotherm event with onset at 81.0° C. and peak at 83.4° C. ΔH 76.4 Jg$^{-1}$ TGA: no marked events between room temperature and 160° C.

Or an alternative for [5-(5-Ethoxymethoxy-benzofuran-2-yl)-6-nitro-pyridin-2-yl]-methyl-carbamic acid tert-butyl ester (13)

j) [5-(5-Ethoxymethoxy-benzofuran-2-yl)-6-nitro-pyridin-2-yl]-methyl-carbamic acid tert-butyl ester (13)

To a degassed solution of 5-ethoxymethoxy-benzofuran boronic acid (4) (0.69 g, 2.63 mmol) in ethanol (17.5 mL), (5-bromo-6-nitro-pyridin-2-yl)-methyl-carbamic acid tert-butyl ester 12 (0.50 g, 1.51 mmol), Pd(PPh$_3$)$_2$Cl$_2$ (0.14 g, 0.20 mmol) and Et$_3$N (0.48 mL, 3.46 mmol) were added. The reaction mixture was stirred at 90° C. for 30 minutes. The reaction mixture was cooled to 0° C. and clear filtered. Volatiles were removed under reduced pressure. The residue was diluted with water and the mixture was extracted with ethyl acetate. The organic extract was washed with brine and concentrated under reduced pressure. The crude product was purified by flash column chromatography. Evaporation of solvent gave title compound 13 (58% yield).

$^1$H NMR (400 MHz, acetone) δ ppm: 8.48 (d, J=8.59 Hz, 1H), 8.36 (d, J=8.98 Hz, 1H), 7.48 (d, J=8.98 Hz, 1H), 7.37 (d, J=2.73 Hz, 1H), 7.23 (s, 1H), 7.09 (dd, J=8.98, 2.34 Hz, 1H), 5.28 (s, 2H), 3.74 (q, J=7.02 Hz, 2H), 3.43 (s, 3H), 1.58 (s, 9H), 1.19 (t, J=7.02 Hz, 3H)

ESMS: m/z 444.44 [M+1]$^+$; 388.45 [(M−56)+1]$^+$

TABLE 2

Representative X-Ray Powder Diffraction peaks for [5-(5-Ethoxymethoxy-benzofuran-2-yl)-6-nitro-pyridin-2-yl]-methyl-carbamic acid tert-butyl ester.

| Angle 2-Theta (2θ) Cu Kα | Relative Intensity |
|---|---|
| 6.18 | vs |
| 9.14 | vw |
| 11.67 | w |
| 12.32 | w |
| 14.65 | w |
| 14.98 | vw |
| 16.44 | w |
| 17.52 | w |
| 20.66 | w | vs = very strong
s = strong
w = weak
vw = very weak

Radiolabelling Example 1

Procedure for the preparation of [$^{18}$F](2-(2-$^{18}$F-fluoro-6-(methylamino)pyridin-3-yl)benzofuran-5-ol from [5-(5-Ethoxymethoxy-benzofuran-2-yl)-6-nitro-pyridin-2-yl]-methyl-carbamic acid tert-butyl ester $^{18}$F-Fluoride was isolated on-line from the cyclotron target solution on a QMA SepPak Light cartridge (Waters) that had been pre-conditioned with aqueous potassium carbonate (0.5 M, 10 mL) and water (18 MΩ, 15 mL). After 3 min, the QMA SepPak light was flushed with a 2 mL portion of a solution of kryptofix (4,7,13,16,21,24-hexaoxa-1,10-diazobicyclo[8.8.8]hexacosane) (99 mg, 0.26 mmol) and potassium carbonate (16 mg, 0.12 mmol) in water (0.85 mL) and dry acetonitrile (20 mL). The eluate was heated at 160° C. under nitrogen flow (110 mL/min) until dry, cooled to RT and a solution of tert-butyl 5-(5-(ethoxymethoxy)benzofuran-2-yl)-6-nitropyridin-2-yl(methyl)carbamate (3 mg, 6.8 μmol) in DMSO (1 mL) was added. The mixture was heated at 85° C. for 15 min, then cooled to 70° C. and hydrochloric acid (6M, 0.25 mL) was added. After 30 min, the reaction mixture was diluted with water (0.5 mL) and loaded onto a semi-preparative HPLC column (ACE C-18 column, 5*250 mm, 5 µm), which was eluted with MeOH/HCO$_2$NH$_4$ (0.1M) (50:50 (v/v)) at 6 mL/min. The fraction eluting at 34 min was collected, evaporated to dryness, the residue was redissolved in a mixture of phosphate buffered saline (pH 7.4) and ethanol (70%) in propylene glycol, 5:3 (v/v) and filtered through a sterile filter (0.22 µm, Millipore). Estimated radiochemical yield: 3%. Radiochemical Purity (HPLC): >99%. MS/MS spectrum of product complies with spectrum from authentic unlabelled 2-(2-fluoro-6-methylamino-pyridin-3-yl)-benzofuran-5-ol.

Unlabeled 2-(2-fluoro-6-methylamino-pyridin-3-yl)-benzofuran-5-ol display an IC$_{50}$ of 13 nM in the competition binding assay described in WO2007/086800.

Procedure for the preparation of [$^{18}$F]2-(6-fluoro-5-methylamino-2-pyridyl)benzofuran-5-ol from tert-butyl N-[6-[5-(ethoxymethoxy)benzofuran-2-yl]-2-nitro-3-pyridyl]-N-methyl-carbamate $^{18}$F-Fluoride was isolated on-line from the cyclotron target solution on a QMA SepPak Light cartridge (Waters) that had been pre-conditioned with aqueous potassium carbonate (0.5 M, 10 mL) and water (18 MΩ, 15 mL). After 3 min, the QMA SepPak light was flushed with a 2 mL portion of a solution of kryptofix (4,7,13,16,21,24-hexaoxa-1,10-diazobicyclo [8.8.8]hexacosane) (99 mg, 0.26 mmol) and potassium carbonate (16 mg, 0.12 mmol) in water (0.85 mL) and dry acetonitrile (20 mL). The eluate was heated at 160° C. under nitrogen flow (110 mL/min) until dry, cooled to RT and a solution of tert-butyl 6-(5-(ethoxymethoxy)benzofuran-2-yl)-2-nitropyridin-3-yl(methyl)carbamate (2.7 mg, 0.26 mmol) in acetonitrile (1 mL) was added. The mixture was heated at 85° C. for 15 min, then cooled to 70° C. and hydrochloric acid (2M, 1 mL) was added. After 30 min, the reaction mixture was diluted with water (0.5 mL) and loaded onto a semi-preparative HPLC column (Waters µBondapak C-18 column, 7.8*300 mm, 10 µm), which was eluted with MeOH/HCO$_2$NH$_4$ (0.1M) (30:70 (v/v)) at 6 mL/min. The fraction eluting at 24 min was collected, evaporated to dryness, and the residue was redissolved in phosphate buffered saline (pH 7.4) and filtered through a sterile filter (0.22 µm, Millipore). Radiochemical yield: 11%. Radiochemical Purity (HPLC): >99%. MS/MS spectrum of product complies with spectrum from authentic unlabelled 2-(6-fluoro-5-methylamino-2-pyridyl)benzofuran-5-ol.

Unlabeled 2-(6-fluoro-5-methylamino-2-pyridyl)benzofuran-5-ol an IC$_{50}$ of 44 nM in the competition binding assay described in WO2007/086800.

The invention claimed is:

1. A compound or salt thereof, wherein the compound is [5-(5-ethoxymethoxy-benzofuran-2-yl)-6-nitro-pyridin-2-yl]-methyl-carbamic acid tert-butyl ester.

2. The compound or salt thereof according to claim 1, wherein the compound or salt is in crystalline form.

3. The compound or salt thereof according to claim 2, wherein the crystalline form exhibits at least one endothermic event with onset between 70° C. and 300° C.

4. The compound or salt thereof according to claim 2, wherein the crystalline form exhibits an X-ray powder diffraction pattern comprising at least one specific diffraction peak at about 2-theta=6.18°.

5. The compound or salt thereof according to claim 2, wherein the crystalline form exhibits the following diffraction peaks: 6.18, 9.14, 11.67, 14.98, and 16.44° 2-theta.

\* \* \* \* \*